United States Patent [19]
della Valle et al.

[11] Patent Number: 5,264,422
[45] Date of Patent: * Nov. 23, 1993

[54] ESTERS OF ALGINIC ACID WITH STEROIDAL ALCOHOLS

[75] Inventors: Francesco della Valle, Padua; Aurelio Romeo, Rome, both of Italy

[73] Assignee: Fidia S.p.A., Abano Terme, Italy

[*] Notice: The portion of the term of this patent subsequent to Jul. 25, 2006 has been disclaimed.

[21] Appl. No.: 718,446

[22] Filed: Jun. 20, 1991

Related U.S. Application Data

[62] Division of Ser. No. 66,133, Jun. 24, 1987, abandoned.

[30] Foreign Application Priority Data

Jun. 30, 1986 [IT] Italy ............................. 48201 A/86

[51] Int. Cl.$^5$ ................ A61K 31/705; A61K 31/72; C08B 37/04
[52] U.S. Cl. ........................................ 514/26; 514/54; 514/171; 514/178; 536/3; 536/123; 536/123.1; 536/5; 536/115; 536/119; 424/423; 424/443; 424/447
[58] Field of Search ................. 514/54, 171, 26, 178; 536/3, 123, 5, 124, 115, 119, 123.1; 424/423, 443, 447

[56] References Cited

U.S. PATENT DOCUMENTS

| | | | |
|---|---|---|---|
| 2,158,487 | 5/1939 | Preble | 536/3 |
| 2,426,125 | 8/1947 | Steiner | 536/3 |
| 2,463,824 | 3/1949 | Steiner et al. | 536/3 |
| 2,477,861 | 8/1949 | Clark et al. | 536/3 |
| 2,478,988 | 8/1949 | Wallerstein et al. | 536/3 |
| 2,494,912 | 1/1950 | Steiner et al. | 536/3 |
| 2,647,035 | 7/1953 | Cramer, Jr. et al. | 536/3 |
| 2,694,058 | 11/1954 | Berger | 536/3 |
| 2,860,130 | 11/1958 | McNeely et al. | 536/3 |

(List continued on next page.)

FOREIGN PATENT DOCUMENTS

| | | | |
|---|---|---|---|
| 0499026 | 1/1954 | Canada | 536/3 |
| 2046966 | 9/1970 | Fed. Rep. of Germany . | |
| 2161415 | 6/1972 | Fed. Rep. of Germany . | |
| 2529086 | 1/1976 | Fed. Rep. of Germany . | |
| 2641303 | 3/1977 | Fed. Rep. of Germany . | |
| 3017221 | 11/1980 | Fed. Rep. of Germany . | |
| 2247204 | 5/1975 | France . | |
| 2418821 | 9/1979 | France . | |
| 47-47858 | 2/1972 | Japan . | |
| 70069 | 6/1980 | Romania . | |
| 0768309 | 2/1957 | United Kingdom | 536/3 |
| 0833946 | 5/1960 | United Kingdom | 536/3 |
| 0962483 | 7/1964 | United Kingdom | 536/3 |
| 0976301 | 11/1964 | United Kingdom | 536/3 |
| 1395898 | 5/1975 | United Kingdom | 536/3 |

OTHER PUBLICATIONS

March; *Adv. Org. Chem.* pp. 367-368 (1977).
Jaeanloz, "The Methyl Ester of Methylated Hyaluronic Acid" in Studies on Hyaluronic Acid and Related Substances VI pp. 141-150 (1952).
Chemical Abstracts, vol. 94, No. 22, Jun. 1st 1981, p. 82, Abstract No. 176606g.
Zeit. Physiol. Chemie 293, 121 (1953).
A. B. Steiner, Industrial and Engineering Chemistry, vol. 43, pp. 2073-2077, (1951).
The Polysaccharides, vol. 2, pp. 411-491, (1985).
"Martindale"—The Extra Pharmacopoeia, 27th Edition, pp. 929-930.
"Martindale"—The Extra Pharmacopoeia, 28th Edition, pp. 960-961.

*Primary Examiner*—Nancy S. Husarik
*Attorney, Agent, or Firm*—Birch, Stewart, Kolasch & Birch

[57] ABSTRACT

Partial esters of alginic acid and salts thereof possess important bioplastic and pharmaceutical qualities and are useful in various fields including medical, surgical, cosmetics and foods.

3 Claims, No Drawings

U.S. PATENT DOCUMENTS

| | | | |
|---|---|---|---|
| 3,108,042 | 10/1963 | Murphy et al. | 536/3 |
| 3,115,488 | 12/1963 | Alburn | 536/3 |
| 3,332,933 | 7/1967 | Schweiger | 536/3 |
| 3,351,581 | 11/1967 | Schweiger | 536/114 |
| 3,450,814 | 6/1969 | Bechtold et al. | 536/3 |
| 3,535,308 | 10/1970 | Schaefer et al. | 536/3 |
| 3,574,641 | 4/1971 | O'Connell et al. | 536/3 |
| 3,772,266 | 11/1973 | Pettitt et al. | 536/3 |
| 3,787,389 | 1/1974 | Negrevergne | 536/17.4 |
| 3,790,558 | 2/1974 | Negrevergne | 536/2 |
| 3,792,164 | 2/1974 | Bechtold | 536/3 |
| 3,824,997 | 7/1974 | Franklin et al. | 536/3 |
| 3,849,341 | 11/1974 | Lamberti | 252/546 |
| 3,887,175 | 6/1975 | Cochard et al. | 536/3 |
| 3,946,110 | 3/1976 | Hill | 514/161 |
| 3,948,881 | 4/1976 | Strong | 536/3 |
| 3,967,618 | 7/1976 | Zaffaroni | 424/424 |
| 3,993,073 | 11/1976 | Zaffaroni | 424/432 |
| 4,002,731 | 1/1977 | Skulan | 424/5 |
| 4,003,792 | 1/1977 | Mill et al. | 530/303 |
| 4,013,820 | 3/1977 | Farhadieh et al. | 536/64 |
| 4,024,073 | 5/1977 | Shimizu | 536/22 |
| 4,104,460 | 8/1978 | Hasebe | 536/3 |
| 4,178,361 | 12/1979 | Cohen et al. | 424/487 |
| 4,206,301 | 6/1980 | Yolles | 536/3 |
| 4,216,104 | 8/1980 | Gergely | 252/91 |
| 4,272,393 | 6/1981 | Gergely | 252/91 |
| 4,330,338 | 5/1982 | Banker | 424/480 |
| 4,364,929 | 12/1982 | Sasmor et al. | 424/80 |
| 4,500,676 | 2/1985 | Balazs et al. | 525/54.2 |
| 4,512,987 | 4/1985 | Schindlery | 514/171 |
| 4,524,064 | 6/1985 | Nambu | 514/778 |
| 4,761,401 | 8/1988 | Couchman et al. | 536/4.1 |
| 4,808,707 | 2/1989 | Daly et al. | 536/3 |
| 4,814,176 | 3/1989 | Makino et al. | 424/468 |
| 4,818,751 | 4/1989 | Ibe | 514/54 |
| 4,851,521 | 7/1989 | della Valle et al. | 514/54 |
| 4,892,659 | 1/1990 | Shibata et al. | 536/119 |
| 4,963,666 | 10/1990 | Malson | 536/55.1 |
| 4,965,353 | 10/1990 | della Valle et al. | 514/54 |

ESTERS OF ALGINIC ACID WITH STEROIDAL ALCOHOLS

This application is a divisional of application Ser. No. 07/066,133, filed on Jun. 24, 1987, now abandoned, the entire contents of which are hereby incorporated by reference.

BACKGROUND AND SUMMARY OF THE INVENTION

The invention concerns alginic acid esters in which all or only some of the carboxylic groups of the acid are esterified, and the salts of the partially esterified acid with metals or organic bases which are acceptable from a pharmacological point of view.

The compounds possess interesting and valuable bioplastic and pharmaceutical qualities and may be used in numerous fields, from cosmetics to surgery and medicine. The invention also includes pharmaceutical preparations containing as an active ingredient one or more alginic acid esters or one of their salts as described above, as well as medicaments containing:

1) a pharmacologically active substance or an association of pharmacologically active substances and,
2) a carrying vehicle comprising a totally or partially esterified alginic acid.

The invention also includes various uses of alginic esters or the above mentioned medicaments, such as in the fields of medicine, surgery or cosmetics and a new procedure for the preparation of alginic acid esters.

Alginic acid is a natural acidic polysaccharide extracted above all from so-called brown algae (Phaecophyceae) with a high molecular weight varying between about 30,000 and 200,000, and containing chains formed by D-mannuronic acid and L-guluronic acid. The degree of polymerization varies according to the type of alga used for extraction, the season in which the algae were gathered and the place of origin of the algae, as well as the age of the plant itself. The main species of brown algae used to obtain alginic acid are, for example, *Macrocystis pyrifera, Laminaria cloustoni, Laminaria hyperborea, Laminaria flexicaulis, Laminaria digitata, Ascophyllum nodosum, Fucus serratus.*

Alginic acid is found in these algae as an extensive constituent of the cell walls in the form of a mixture of some of its alkaline salts, of these especially sodium salt. This mixture is also known as "algin". These salts are normally extracted in aqueous conditions with a sodium carbonate solution and it is possible to obtain alginic acid directly from this extract by precipitation with an acid, for example a mineral acid such as hydrochloric acid. An indirect preparation procedure involves first making an insoluble calcium salt by adding a soluble calcium salt, such as chloride, and after washing this salt, alginic acid is obtained again by treatment with an acid.

Alginic acid or alkaline alginates may, however, also be obtained microbiologically, for instance by fermentation with *Pseudomonas aeruginosa* or mutants of *Pseudomonas putida, Pseudomonas fluorescens* or *Pseudomonas mendocina.*

The metal salts of alginic acid, especially the alkaline and alkaline earth metal salts, have interesting chemical and physical properties and are therefore widely used in industry, Thus, for example, the solutions of alkaline or alkaline earth alginates are extremely suitable, due to their viscosity, and their adjustability by temperature and pH, for the preparation of gels which may be widely used in the food industry, for the preparation of ice creams, milk puddings and many other types of cakes and puddings. Another property which is widely exploited in the field of alimentation is the ability of alginates to retain water, and for this reason they are used for example for the conservation of many types of frozen foods. A third property of alginates is their power to emulsify and to stabilise emulsions; for this reason too these salts are important in the food industry, where they are used for the preparation of condiments and for the stabilisation of many types of drink, such as beer or fruit juices, sauces and syrups.

The ability of alginate solutions to form films and fibres has been exploited in the paper industry, in making adhesive labels, in textile printing and dyeing, and in the preparation of sanitary, medical and surgical articles. Alginates are used as emulsifiers for the preparation of polishes, antifoam agents, lactics and as stabilisers in the ceramic and detergent industries (for a more detailed list see for example "The Polysaccharides", Vol. 2, by Paul A. Sandford and John Baird, Copyright 1983 by Academic Press., Inc.).

Alginic acid and its salts have also been used however in the pharmaceutical, medical, surgical and cosmetic fields, for example for the preparation of medicaments for topical use and sanitary and surgical articles. For example the German Offenlegungsschrift 3 017 221 (20.11.1980), discloses an "artificial skin" for use in serious lesions of the skin, for example following burns, in which an ointment containing a soluble alginate of an alkaline metal is applied topically to the skin and treated in situ with a soluble calcium salt. This causes the formation of insoluble calcium alginate, transforming the layer of ointment into an easily tolerated biologically protective film, with structural and mechanical physical characteristics similar to those of natural skin.

Calcium alginate has been used for the manufacture of fibres for use in the pharmaceutical industry French patent application No. 2.418 821 (28.9.1979), Rumanian Patent No.70 069 (30.6.1980) contains the description of a healing and antiseptic medicament for skin wounds, made from calcium alginate fibres. Calcium alginate is also used as a hemostatic agent in the form of bandages or gauses containing fibres of the salt. Other medicaments based on calcium alginate are used for the treatment of sinoids, fistulas, and in the treatment of nosebleeds. In Galenism, sodium and calcium alginates are also used as disintegrators for pills, and sodium alginate is also used for its binding properties.

Also used in industry in many of the abovementioned fields are two alginic acid esters or salts of such esters, more precisely ethylene glycol and propylene glycol esters. The latter is used for example as an emulsifier and stabiliser for foodstuffs. (See for example "Martindale"- The Extra Pharmacopoeia, p. 931 and "The Polysaccharides", Vol. 2, Copyright by Academic Press, Inc. 1983, pp. 448–449). The above mentioned esters have been obtained by reaction of alginic acid, or its salt or partial salt, with ethylene or propylene oxide respectively. This preparation method is also the basis of patents for the preparation of the above mentioned alginic acid esters and esters of bivalent alcohols by reaction of an aliphatic hydrocarbon epoxide, possibly substituted or interrupted by hetero atoms in the carbon atom chain (see for example U.S. Pat. Nos. 2,463,824-2,426,125-2,463,824, German Offenlegungsschriften 2,161,415-2,046,966-2,641,303-2,529,086, Japanese Patent Nos. 2027 ('59) and 72 47 858, and French Patent No. 2247204.

The alginic acid esters obtainable by the action of the above mentioned epoxides on the free acid or its salts are partial esters (see A. B. Steiner, Industrial and Engineering Chemistry, Vol.43, pp. 2073-2077, 1951), with a maximum degree of esterification of about 80% of all the existing carboxylic groups in the case of glycol esters with a low molecular weight, and a very low degree in the case of glycol esters with long chains. It has not been possible until now to prepare total esters by this method.

Monovalent alcohol esters, both aliphatic and araliphatic have also been mentioned in literature, above all a methyl ester of alginic acid obtained by reaction of alginic acid in an ethereal solution of diazomethane. (Zeitschrift fuer physiologische Chemie, Vol. 293, p. 121, 1953, A. B. Steiner, Industrial and Engineering Chemistry, Vol. 43, p. 2073, 1951, U.K. Patent No. 768,309. It seems however that the products obtained by reaction with diazomethane are not really alginic acid esters but rather methyl esters of an alginic acid partially etherified to the hydroxy alcohol groups, as described for example in Example 4 of the above mentioned U.K. patent. One methyl ester has also been obtained by reaction of dimethyl sulphate on a soluble salt of alginic acid in an organic solvent with low solubility in water, but in the presence of water (U.S. Pat. No. 2,860,130). The product obtained, referred to as methyl alginic acid or methyl alginate, is not to be considered as a pure ester, since it is known that sugar hydroxyls are easily etherified with this methylating agent. This case, therefore, also is truly a mixed ester-ether.

Also mentioned in literature are alginic acid esters of monovalent alcohols, with no indication however of their preparation method and no description of their chemical and physical properties. As no preparation method is known, apart from the above mentioned reaction with diazomethane and dimethyl sulphate, it is probable that the use of homologues of these esterifying agents to obtain esters of the homologous series of the methyl ester are not practical at all, or at the most they result in mixed products, as in the case of methyl products. (See for example U.S. Pat. No. 4,216,104 in which a propyl alginate is mentioned with no indication of its origin or preparation method, and the Japanese Kokai No. 55-132781, page 5, in which ethyl, butyl, lauryl, oleyl, phenyl and benzyl esters are mentioned, with no indication as to how they are obtained).

On the basis of these facts therefore, it is presumed that of all alginic acid esters only those esters of bivalent alcohols are known, and more precisely only alginic acid partially esterified with glycols, since by the known method used in industry, it is difficult to achieve complete esterification and in the commercial product no less than 10% of the carboxyls remain unesterified in their free carboxy form, possibly salified.

OBJECTS AND SUMMARY OF THE INVENTION

The main object of the invention is therefore the new alginic esters, such as those already mentioned, and the new procedure for their preparation.

The present invention concerns new polysaccharide esters and more precisely alginic acid esters and methods for their preparation.

The invention also includes the use of these alginic acid esters (or alginic esters) in the food, paper, textile, and cosmetic industries, in the pharmaceutical sector, in medicine and surgery and also includes, therefore, new articles containing alginic acid esters for use in these various industrial sectors, for example, foodstuffs, cosmetic articles, pharmaceutical preparations, biodegradable plastic materials for medical-surgical use. The new esters according to the invention include alginic acid totally and partially esterified, hereafter called total alginic acid esters and partial esters. In the partial esters the nonesterified carboxylic groups may be salified with metals or organic bases, and these salts, as indeed the industrial articles which contain them, form part of the invention.

DETAILED DESCRIPTION OF THE INVENTION

The present invention includes a simple and very convenient procedure for the preparation of alginic esters, based on the treatment of quaternary ammonium salts of alginic acid with conventional alkylating agents in organic, preferably aprotic, solvents, such as in dimethylsulfoxide, making a large number of new alginic esters available, especially those esters of monovalent alcohols, such as homologues of methyl ester, and esters of aromatic, araliphatic, alicyclic and heterocyclic alcohols. The new procedure may be used also for the preparation of esters deriving from substituted alcohols, in particular known esters of bivalent aliphatic alcohols, obtainable by the reaction of alginic acid with aliphatic epoxides, as described above, and mainly new total esters of such bivalent alcohols.

The new alginic esters may be used in various sectors of industry and in the pharmaceutical, sanitary, surgical and cosmetic fields, where metal alginates or the esters of aliphatic bivalent alcohols of the type of propyleneglycol ester of alginic acid are already used, for example in the food or cosmetic industries. Therefore, part of the invention is represented by both this use of the new esters, and the corresponding articles and industrial products, such as cosmetic, sanitary, surgical and pharmaceutical articles, or food products and their auxiliaries, especially emulsifying agents, emulsion stabilisers, and thickening agents and possibly related uses.

With the discovery of the new alginic esters according to the present invention, a new use for alginic esters in general has also come to light, that is for the new esters and those already known. This new use is their use as vehicles for pharmaceutically active substances, especially those with a topical, oral or rectal action, but also those for parenteral administration. The use of known alginic esters of bivalent alcohols was limited to the function of emulsifying agents, emulsion stabilisers, thickening agents and possibly related uses. No use in the pharmaceutical, sanitary, medical, surgical or cosmetic fields was envisaged for those esters. The present invention therefore concerns also the above mentioned use and respective products, especially the pharmaceutical preparations containing an alginic ester as vehicle for the active substances.

The active substance may also be vehicled by the new esters which have a pharmacologically active substance as their alcohol component. Of the pharmaceutical preparations of the present invention, therefore, particularly interesting are those containing an alginic ester deriving from a therapeutically active alcohol, such as those mentioned hereafter, that is, esters comprised of alginic acid esterified with the alcohol moiety of a therapeutically active compound.

The invention also includes partial alginic esters with metals or organic bases. In the following description, where the meaning does not exclude this, the terms "alginic acid esters" or "alginic esters" shall be taken to mean both the esters themselves and their above mentioned salts. In particular, in the above mentioned pharmaceutical preparations, one or more pharmacologically active substances may be vehicled, apart from by pharmacologically active or inactive alginic esters, also by pharmacologically active basic substances used to salify part or all the free carboxyl groups of partial alginic esters.

The use of the above mentioned alkaline alginates in the various sectors of industry, pharmaceutics, surgery and above all in the food industry, presents some disadvantages when they are used in acid conditions, because of the resulting release of alginic acid with low solubility which may separate in the solid state. Also in the presence of calcium ions, some insoluble products containing calcium alginate may separate, and for this reason alkaline alginates are unsuitable for use in liquids containing the above mentioned ions, for example in products containing milk or milk derivatives.

For this reason the above mentioned soluble salts of alginic acid have been substituted by the aforesaid glycol esters, especially propyleneglycol ester, in those cases in which it is essential to maintain a good level of solubility also in acid conditions or in the presence of calcium salts, such as when the alginate is used as emulsifier or emulsion stabiliser, for example for beer or fruit juices. The glycol esters of alginic acid are however toxic to a certain extent and their use must be limited. This is due to the intrinsic toxicity of the glycol residue, the part which is absorbed and metabolised.

The present invention makes available to the aforesaid various industrial and scientific fields an assortment of new products with properties essentially similar to those of alkaline alginates or the already known glycol esters, but with effects which are more in keeping with the requirements of increasingly perfected products, and these effects naturally vary from case to case according to the use to which the new products are put. It is important to underscore, first and foremost, the superiority of the monovalent esters according to the present invention over and above the known glycol esters, since the monovalent alcohol residues are metabolised in the organism to degraded products which are less toxic than the glycols. This is naturally true of esters deriving from alcohols which do not contain toxic substitutes, such as especially aliphatic, cycloaliphatic, monovalent alcohols. These new esters will be of great advantage above all in the food industry for the uses mentioned previously.

The low level of toxicity of the esters of numerous monovalent alcohols of alginic acid according to the present invention may be exploited mainly in the pharmaceutical, cosmetic and sanitary-surgical fields where the new alginic esters may be used as biodegradable plastic materials with various functions as the case may be. Thus, for example, the alginic esters may be used as additives for the wide range of polymeric materials used for sanitary and surgical articles, such as polyurethanes, polyesters, polyolefins, polyamides, polysiloxanes, vinyl and acrylic polymers, with the effect of rendering these materials biocompatible. In this case the addition of an alginic ester is carried out for example by coating the surface of these materials or by dispersion in the same or by a combination of both procedures. These materials may be used for the manufacture of various sanitary and medical articles such as cardiac valves, intraocular lenses, vascular clips, pace-makers and the like, including these types of articles discussed in U.S. Pat. No. 4,500,676.

In the cosmetic and pharmaceutical fields, the alginic esters of the invention may be used for the preparation of ointments, creams and other types of medicaments for topical application or cosmetic products, such as sunshield creams, where they act as stabilisers and emulsifiers having a greater degree of stability than alkaline alginates, especially with regard to higher temperatures, and a lesser degree of toxicity compared to glycol esters. In pharmaceuticals they may be used to the same advantage as disintegrators for pills or as a binding agent, but above all, according to a particularly important aspect of the present invention, as a vehicle for pharmacologically active substances, especially those for topical use. This vehicling action of the new esters may be carried out various ways, specifically including:

1) the alginic ester serves as vehicle and is associated mechanically, physically mixed with the active substance;
2) the alginic ester (partial) is salified with the active substance; and
3) the alginic ester is esterified with an alcohol which represents the active substance.

Apart from these three variations, combinations of the same may be used, for example a combination (1) and (2); or (1) and (3). In the case of variations (2) and (3), it is possible to vary and combine the alcohol residues in the alginic ester, or the basic component in the salts, and it is possible to have esters of a mixed character, in which the alcohol residues derive partly from pharmacologically inactive alcohols and partly from active alcohols, and the same is true of the salts. It is possible to have in the same ester both inactive basic residues, as in the case of metallic salts, and residues of therapeutically active organic bases.

A first group of esters according to the present invention suitable for use in the above mentioned industrial sectors, such as in the food, paper, textile and printing industries, and in the preparation of sanitary, medical and surgical articles, detergents, household articles, etc., is represented by those esters in which the properties of the alginic component are the properties to be exploited. These esters derive from alcohols of the aliphatic, aromatic, araliphatic, cycloaliphatic or heterocyclic series which have no toxic or pharmacological action, such as for example the saturated alcohols of the aliphatic series or simple alcohols of the cycloaliphatic series. Examples of these alcohols are mentioned hereinafter.

A second group of esters for use in therapy is represented by the esters in which the pharmacological qualities of the alcohol component are dominant, that is, alginic acid esters with pharmacologically active alcohols, such as steroidal alcohols, such as those of the cortisone type. These esters possess properties which are qualitatively similar to those of the alcohol, but with a wider range of action. Even as compared to already known esters of such pharmaceutically active alcohols the alginic esters ensure a more balanced, constant and regular pharmacological action and generally cause a remarkable retard effect of the active alcohol component.

A third group of alginic acid esters according to the present invention, and representing a particularly original and useful aspect of the same, is that of the esters of a more mixed character compared to the two previous groups. That is, esters in which part of the carboxylic groups of alginic acid are esterified with a pharmacologically active alcohol and another part with a pharmacologically indifferent alcohol, or the activity of which is negligible. By suitably dosing the ratio between the two types of alcohol as the esterifying component, it is possible to obtain esters with the same activity as the pharmacologically active alcohol and having those qualities mentioned above of increased stability and bioavailability of the pharmacologically active alcohol.

A fourth group of esters is represented by those of a mixed character in which the ester groups derive from two different therapeutically active substances. In this case also the esters may be partial or total, that is, only some carboxylic groups derive from two different therapeutically active alcohols, for example from a cortisone steroid and from an antibiotic, while the other groups may be free or salified, for example with alkaline metals, above all sodium, or all the carboxylic groups are esterified with the above mentioned alcohols. It is possible however to prepare esters with three or more alcoholic components, for example esters in which a part of the carboxylic groups are esterified with a therapeutically active alcohol, another part with another therapeutically active alcohol, a third part with a therapeutically inactive alcohol and a fourth part is possibly salified with a metal or with a therapeutically active or inactive base, or it is in a free form.

Most of the esters of alginic acid, in contrast to its salts, present a certain degree of solubility in organic solvents. This solubility depends on the percentage of esterified carboxylic groups and on the type of alkyl group bound to the carboxyl. For example, a total ester of alginic acid thus obtained presents at room temperature good solubility, for example, in dimethylsulfoxide. The total esters which are all new and are a particular object of the present invention, present on the other hand poor solubility in water. Thus, for example, the total esters of monovalent alcohols, such as lower and higher alkyl esters, are not very soluble or insoluble in water and aqueous solutions. Also the new total esters of bivalent alcohols, such as the total ester of the glycols, such as ethyleneglycol, propyleneglycol, trimethyleneglycol, butyleneglycol, isobutylenglycol are not very soluble or insoluble in water and aqueous solutions.

These solubility characteristics, together with the marked viscoelastic properties of esters, make them suitable for use in the manufacture of sanitary and medical articles which are insoluble in saline and have the particular desired form. Such articles may be prepared for example by dissolving an ester of alginic acid in an organic solvent, giving the extremely viscous solution the form of the desired article and lastly by extracting the organic solvent with another solvent which can be mixed with the first, but in which the alginic acid ester is insoluble, for example an alcohol or water.

In all the above mentioned esters in which carboxy acid groups remain free, these may be salified with metals or with organic bases, for example with alkaline or alkaline earth metals or with ammonia or azotized organic bases.

The invention includes the industrial use of the new alginic esters in all the aforementioned sectors, especially in the alimentary, cosmetic, pharmaceutical and medical fields, in the manufacture of household and industrial articles, especially for the manufacture of sanitary and surgical articles.

The invention includes also the use of alginic esters in general, that is the new ones and those already described in literature, for the new applications described here, for example their use as vehicles for pharmacologically active substances, both in the form of alginic esters with therapeutically active alcohols, and as alginic esters of inert alcohols to mix with therapeutically active substances, or with therapeutically active bases as well as the pharmaceutical medicaments or preparations resulting from this use of alginic esters. In all cases the free carboxy groups may be salified with inactive but therapeutically acceptable bases.

The invention further includes all the industrial articles or pharmaceutical preparations mentioned above.

The main object of the present invention is therefore represented by the total or partial esters of alginic acid with alcohols of the aliphatic, araliphatic, cycloaliphatic or heterocyclic series and by the salts of such partial esters with inorganic or organic bases, with the exception of the partial esters of bivalent aliphatic alcohols.

A second object of the invention is represented by a new procedure for the preparation of alginic esters characterised by the treatment of a quaternary ammonium salt of alginic acid with an alkylating agent in an aprotic solvent, and, if desired, by the salification of the free carboxy groups with inorganic or organic bases, and the partial alginic esters thus obtained.

A third object of the invention is represented by the use of the new alginic esters and their salts, in substitution of the metal alginates or of the alginates of aliphatic bivalent alcohols, in the respective industrial sectors or in their applications in the cosmetic, pharmaceutical or sanitary-surgical fields, and by the respective products or industrial articles.

A fourth object of the invention is represented by the use of alginic esters as vehicles for pharmaceutically active substances and by pharmaceutical preparations or medicaments containing:

1) a pharmacologically active substance or an association of pharmacologically active substances; and
2) a carrying vehicle containing a total or partial ester of alginic acid or salts of such partial esters with inorganic or organic bases, or pharmaceutical preparations or medicaments containing an alginic ester possibly salified with inorganic or organic bases, in which at least one ester group or a salified carboxy group derives from an alcohol or respectively from a therapeutically active base.

Alcohols Useful in Making the New Esters

Alcohols of the aliphatic series for use as alkylating components of the carboxy groups of alginic acid according to the present invention are, for example, those with a maximum of 34 carbon atoms, which may be saturated or unsaturated and which may possibly also be substituted by other free or functionally modified groups, such as amino, hydroxy, aldehydo, keto, mercapto, carboxy groups or by groups deriving from the same, such as hydrocarbyl or dihydrocarbylamino (hereafter the term "hydrocarbyl" should be taken to mean not only monovalent radicals of hydrocarbons such as the $C_nH_{2n+1}$ type, but also bivalent or trivalent radicals, such as "alkylenes"—$C_nH_{2n}$—or "alkylidenes"=$C_nH_{2n}$), ether or ester groups, acetal or ketal groups, thio-ether or thioester groups and esterified carboxy groups or carbamidic or carbamidic groups substituted by one or two hydroxy groups, by nitrile groups or by halogens.

In the above groups containing hydrocarbyl radicals these are preferably lower aliphatic radicals, such as alkyls, with a maximum of 6 carbon atoms. These alcohols may also be interupted in the carbon atom chain by heteroatoms, such as oxygen, nitrogen and sulfur. Preference is given to alcohols substituted with one or two of the aforesaid functional groups.

Alcohols of the above group to be used preferentially within the terms of the present invention are those with a maximum of 12 and especially with a maximum of 6 carbon atoms and in which the hydrocarbyl radicals in the above mentioned amino, ether, ester, thioether, thioester, acetal, ketal groups representing alkyl groups with a maximum of 4 carbon atoms, and also in the esterified carboxy or substituted carbamidic groups the hydrocarbyl groups are alkyls with the same number of carbon atoms, and in which the amino or carbamidic groups may be alkyleneamino or alkylenecarbamidic groups with a maximum of 8 carbon atoms. Of these alcohols those to be mentioned first and foremost are the saturated and unsubstituted ones such as methyl, ethyl, propyl, isopropyl alcohols, n-butyl alcohol, isobutyl, tert-butyl alcohols, amyl, pentyl, hexyl, octyl, nonyl, and dodecyl alcohols and above all those with a linear chain such as n-octyl or n-dodecyl alcohols. Of the substituted alcohols of this group the bivalent alcohols should be listed, such as ethyleneglycol, propylene glycol or butylene glycol, the trivalent alcohols such as glycerin, aldehydo alcohols such as tartronic alcohol, carboxy alcohols such as lactic acids, for example α-oxypropionic acid, glycolic acid, malic acid, tartaric acids, citric acid, aminoalcohols, such as aminoethanol, aminopropanol, n-aminobutanol and their dimethyl and diethyl derivatives in the aminic function, choline, pyrrolidinylethanol, piperidinylethanol, piperazinylethanol and the corresponding derivatives of n-propyl or n-butyl alcohols, monothioethyleneglycol or its alkyl derivatives, for example the ethyl derivative in the mercapto function.

Of the higher saturated aliphatic alcohols, those worthy of special mention are for example cetyl alcohol and myristyl alcohol, but especially important for the purposes of the present invention are the higher unsaturated alcohols with one or two double bonds, such as especially those contained in many essential oils and having an affinity with terpenes such as citronellol, geraniol, nerol, nerolidol, linalool, farnesol, phytol.

Of the lower unsaturated alcohols consideration should be given to propargyl alcohol.

Of the araliphatic alcohols those to be mentioned above all are those with only one benzene residue and in which the aliphatic chain has a maximum of 4 carbon atoms, in which also the benzene residue may be substituted by between 1 and 3 methyl or hydroxy groups or by halogen atoms, especially chlorine, bromine or iodine and in which the aliphatic chain may be substituted by one or more functional groups selected from the group consisting of free amino groups or mono-or dimethyl groups or by pyrrolidine or piperidine groups.

Of these alcohols, benzyl alcohol and phenethyl alcohol are especially preferred.

The alcohols of the cycloaliphatic or aliphatic cycloaliphatic series may derive from mono or polycyclic hydrocarbons and may have a maximum of 34 carbon atoms. Of the alcohols derived from cyclic monocyclic hydrocarbons special mention should be given to those with a maximum of 12 carbon atoms, with rings containing preferably between 5 and 7 carbon atoms, possibly substituted for example by between one and three lower alkyl groups, such as methyl, ethyl, propyl or isopropyl groups. Specific alcohols of this group are cyclohexanol, cyclohexanediol, 1, 2, 3 cyclohexanetriol and 1, 3, 5 cyclohexanetriol (phloroglucitol), inositol, the alcohols deriving from p-menthane such as. carvomenthol, menthol, α and γ-terpineol, 1-terpineol, 4-terpineol and piperitol, or a mixture of these alcohols known as "terpineol", 1,4-and 1,8-terpin. Alcohols deriving from hydrocarbons with condensed rings are, for example, those of the thujane, pinane, camphane groups, particularly thujanol, sabinol pinol hydrate, D and L-borneol and D and L-isoborneol.

Polycyclic aliphatic cycloaliphatic alcohols for use in obtaining the esters of the present invention are sterols, cholic acids and steroids, such as sexual hormones and the synthetic analogues, in particular corticosteroids and their derivatives. Thus for example it is possible to use: cholesterol, dihydrocholesterol, epidihydrocholesterol, coprostanol, epicoprostanol, sitosterol, stigmasterol, ergosterol, cholic acid, deoxycholic acid, lithocholic acid, estriol, estradiol, equilenin, equilin and their alkyl derivatives, as well as their ethynyl propynyl derivatives in position 17, for example 17-α-ethynyl-estradiol or 7-α-methyl-17α-ethynyl-estradiol, pregnenolone, pregnanediol, testosterone and its derivatives, such as 17-α-methyltestosterone, 1,2-dehydrotestosterone and 17α-methyl-1,2-dehydrotestosterone, the alkyl derivatives in position 17 of testosterone and of 1,2-dehydrotestosterone, such as 17α-ethynyltestosterone, 17 α-propynyltestosterone, norgestrel, hydroxyprogesterone, corticosterone, deoxycorticosterone, 19-nortestosterone, 19-nor-17α-methyltestosterone and 19-nor-17α-ethynyltestosterone, cortisone, hydrocortisone, prednisone, prednisolone, fludrocortisone, dexametasone, betamethasone, paramethasone, flumethasone, fluocinolone, fluprednylidene, clobetasol, beclomethasone, aldosterone, deoxycorticosterone, alphaxolone, alphadolone, bolasterone and anti-hormones such as cyproterone.

Useful as alkylating components for the esters of the present invention are genins (aglycons) of cardioactive glycosides, such as digitoxigenin, gitoxigenin, digoxigenin, strophantidin, tigogenin and saponins.

Other alcohols to be used according to the invention are the vitamin ones, such as axerophthol, vitamins $D_2$ and $D_3$, aneurine, lactoflavine, ascorbic acid, riboflavine, thiamine, pantothenic acid.

Of the heterocyclic alcohols, the following are preferred: furfuryl alcohol, alkaloids and derivatives such as atropine, scopolamine, cinchonine, cinchonidine, quinine, morphine, codeine, nalorphine, N-butyl-scopolammonium bromide, ajmaline; phenylethylamines such as ephedrine, isoproterenol, epinephrine; phenothiazine drugs such as perphenazine, pipothiazine, carphenazine, homofenazine, acetophenazine, fluphenazine, N-hydroxyethyl-promethazine chloride; thioxanthene, drugs such as flupenthixol, clopenthixol; anticonvulsants such as meprophendiol, antipsychotic drugs such as opipramol; antiemetics such as oxypendyl; analgesics such as carbetidine, phenoperidine and methadol; hypnotics such as etodroxizine; anorexics such as benzhydrol and diphemethoxidine; minor tranquilizers such as hydroxyzine; muscle relaxants such as cinnamedrine, cardiphylline, mephenesin, methocarbamol, chlorphenesin, 2,2-diethyl-1,3-1-propanediol guaifenesin, idrocilamide; coronary vasodilatators such as dipyridamole and oxyfedrine; adrenergic blockers such as propanolol, timolol, pindolol, bupranolol, atenolol, metoprolol, practolol; antineoplastics such as 6-azauridine, cytarabine, floxuridine; antiboitics such as chloramphenicol, thiamphenicol, erythromicin, oleandomycin, lincomycin; antivirals such as idoxuridine; peripheral vasodilators such as isonicotinyl alcohol; carbonic anhydrase inhibitors such as sulocarbilate; anti-asthmatics and anti-inflammatories such as tiaramide; sulfamidics such as 2-p-sulfanylanilinoethanol.

The total and partial esters of alginic acid according to the invention have the following general formula:

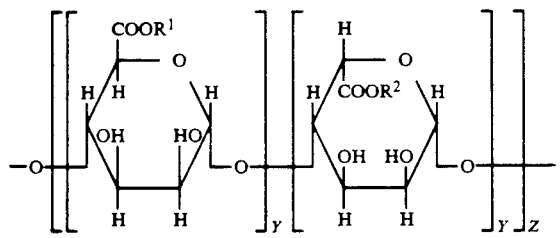

wherein $R^1$ and $R^2$ are each independently hydrogen or an alcoholic moiety selected from the group consisting of aliphatic, araliphatic, cycloaliphatic and heterocyclic radicals and pharmaceutically acceptable salts thereof with the proviso that said partial ester is not a partial ester of a bivalent alcohol.

As discussed above, in some cases alginic acid esters in which the ester groups derive from one or more hydroxy substances with therapeutic action, may be of special interest, and naturally all possible variations of the same. Especially interesting are those substances in which are present two different types of ester groups deriving from drugs of a hydroxy character and in which the remaining carboxy groups are free, salified with metals or with one or several of the bases listed below, possibly also bases which are themselves therapeutically active, for example with the same or a similar activity as that of the esterifying component. In particular, it is possible to have alginic esters deriving on the one hand from an anti-inflammatory steroid, such as one of those mentioned above, and on the other hand from a vitamin, from an alkaloid or from an antibiotic, such as one of those listed here.

The degree of esterification of alginic acid with the above mentioned alcohols depends first and foremost on the special properties desired for the various fields of application. For example a greater or lesser degree of lipophilia or hydrophilia with regard to such tissues, for example the skin. Usually, a high degree of esterification to the point of total esterification of alginic acid increases its lipophilic character and therefore decreases its solubility in water. For a use in therapy of the new esters of this invention, for example, it is of the utmost importance to regulate the degree of esterification in order to ensure, despite good and increased lipophilia compared to metal alginates, a sufficient degree of hydrosolubility, for example a solubility of 10 mg/ml.

Naturally it is necessary to consider also the influence of the molecular size of the same esterifying component, which usually has an inversely proportional influence on hydrosolubility.

As has been said previously, esterification of the carboxy groups of alginic acid may play several roles, to be exploited in various fields, for example in medicine, using the esters as therapeutic agents or in surgery using them as plastic articles. For use in therapy we have already said that esterification of an alcohol can in itself be considered therapeutically active, such as anti-inflammatory corticosteroids for example, with alginic acid as a means of improving therapeutic efficacy.

With regard to similar therapeutically active alcohols alginic acid acts therefore as a particularly efficient vehicle which is perfectly compatible with the biological environment. Many of these pharmacologically active alcohols appear in the above list of alcohols for use in esterification according to the present invention and the possible applications of the corresponding esters therefore are evident, since their indications are the same as those for the free alcohols. Again, as has already been said, in partial esters with therapeutically active alcohols it is possible to esterify part or all of the remaining carboxy groups of the alginic component with pharmacologically inert alcohols, such as for example saturated lower aliphatic alcohols, for example ethyl or isopropyl alcohols.

One particularly interesting aspect of the present invention is the possibility of preparing more stable drugs than those available up till now. It is possible for example to obtain drugs with a "retard" action with alginic esters with therapeutically active alcohols, possibly salified also with therapeutically active bases.

For cosmetic purposes it is preferable to use total or partial esters of alginic acid with pharmacologically inert alcohols, for example saturated or unsaturated aliphatic alcohols, for example unsubstituted alcohols of this type with straight or ramified chains, for example between 1 and 8 carbon atoms, such as those specifically mentioned. Of particular interest also are unsaturated alcohols, for example with one or more double bonds, such as vinyl or allyl alcohols and the condensed derivatives, such as especially polyvinyl alcohol or polyvalent alcohols, such as glycerin. In this case also mixed esters may be used, according to the particular use for which they are intended.

Cycloaliphatic alcohols are also useful, for example those derived from cyclopentane or cyclohexane and from their derivatives substituted by lower alkyl groups, for example alkyls with between 1 and 4 carbon atoms, especially from methyl groups. Particularly interesting are esters with cycloaliphatic and aliphatic-cycloaliphatic alcohols derived from terpenes, such as those mentioned above and from therapeutically active alcohols, which can otherwise be used in cosmetics.

The alcohols to be used preferably for the manufacture of sanitary and surgical articles are essentially the same as those mentioned above for cosmetic use.

In the esters according to the invention the percentage of esterified groups may vary a great deal according to the intended use of the product, and this above all with regard to the use in the various fields of application mentioned above.

Thus, for example, for the manufacture of sanitary-surgical articles it is preferable to use total or partial esters with a high grade of esterification, for example between 80% and 100% of all the carboxy groups present.

Of particular interest also are those partial esters in which at least 5% and at the most 90% of all the carboxy groups of alginic acid are esterified, and especially those with a percentage of between 50 and 80%, to be used preferably for alimentary, cosmetic and pharmaceutical purposes.

In the mixed partial esters the ratio between the number of different types of ester groups may of course vary. For example in the case of two types of such groups, the ratio varies preferably between 0.1:1 and 1:0.1, and this is true also of total esters. For those esters intended for therapeutic purposes the ratio varies preferably between 0.5:1 and 1:0.5. These ratios are also valid in the case of total esters and, in the case of partial esters, are to be taken preferably with reference to the above mentioned percentages regarding the inclusive number of esterified groups.

Basic Compounds Useful in Making Salts of the New Partial Esters

In the partial esters of the invention the nonesterified carboxy groups may be kept free or may be salified. The bases for the formation of these salts are chosen according to the ultimate end use of the product. Inorganic salts may be formed from alkaline metals, such as potassium and in particular sodium and ammonium, or deriving from alkaline earth metals such as calcium or magnesium or aluminium salts.

Of particular interest are the salts with organic bases, especially azotized bases and, therefore, aliphatic, aralipathic, cycloaliphatic or heterocyclic amines. These ammonium salts may derive from therapeutically acceptable amines or nontoxic but therapeutically inactive amines, or from amines with a therapeutic action. Of the first type, preferred are aliphatic amines, for example mono-, di- and tri-alkylamines with alkyl groups with a maximum of 8 carbon atoms or arylalkylamines with the same number of carbon atoms in the aliphaic part and where aryl means a benzene group possibly substituted by between 1 and 3 methyl groups or halogen atoms or hydroxy groups. The biologically inactive bases for the formation of the salts may also be cyclic, such as monocyclic alkyleneamines with cycles of between 4 and 6 carbon atoms, possibly interupted in their cycle by heteroatoms chosen from the group formed by nitrogen, oxygen and sulphur, such as piperazine or morpholine, or may be substituted, for example by amino or hydroxy functions such as aminoethanol, ethylenediamol, ethylenediamine, ephedrine or choline.

It is also possible to form quaternary ammonium salts of partial esters, for example the salts of tetraalkylammonium with the above said number of carbon atoms and preferably salts of this type in which the fourth alkyl group has between 1 and 4 carbon atoms, for example a methyl group.

The biologically active amines to be used for salification and whose therapeutic action may be put to use are all known azotized and basic drugs such as those in the following groups: alkaloids, peptides, phenothiazine, benzodiazepine, thioxanthenes, hormones, vitamins, anticonvulsants, antipsychotics, antiemetics, anesthetics, hypnotics, anorexics, tranquilizers, muscle relaxants, coronary vasodilators, antineoplastics, antibiotics, antibacterials, antivirals, antimalarials, carbonic anhydrase inhibitors, nonsteroid anti-inflammatories, vasoconstrictors, cholinergic agonists, cholinergic antagonists, adrenergic agonists, adrenergic antagonists, narcotic antagonists.

Examples of specific useful drugs are all those drugs mentioned above having azotized basic groups regarding the alginic esters with therapeutically active alcohols or those mentioned hereafter in this text, for example the various antibiotics.

Use of the New Esters as a Drug Vehicle

Salification of the partial esters with the aforesaid therapeutically active bases and the use of such salts represents a particular case of alginic esters functioning as a vehicle, obtainable by the simple addition to the active substance of partial or total esters or their salts with one of the above mentioned therapeutically acceptable but biologically inactive substances, above all with alkaline metals, for example sodium.

The vehicling action of alginic esters therefore opens up possibilities for new medicaments wherein the components are:
1) a pharmacologically active substance or an association or mixture of two or more of such substances; and
2) an alginic ester as described above or one of its salts.

These medicaments are a further object of the invention. The alginic esters for use in these medicaments are above all those in which the esterifying alcohol is itself not pharmacologically active, for, example a simple aliphatic alcohol, as described above. Included in the invention however are medicaments of this type in which the ester is also pharmacologically active, for example in the case of one of the esters described above deriving from pharmacologically active alcohols.

In such medicaments, if partial esters of alginic acid are used, the possible salification of the remaining carboxy groups is carried out preferably with therapeutically neutral inorganic or organic bases, especially with alkaline metals, such as sodium or ammonium. In cases where the active substance (1) or a corresponding association of substances have basic groups, such as for example antibiotics containing amino groups, and if partial esters of alginic acid are used with remaining free carboxy groups, a salt is formed between the free carboxy groups of alginic acid and those basic substances. The basic substance may of course be excessive, thus having basic salts. The new medicaments therefore include in particular the partial esters of alginic acid partially salified with pharmacologically active substances of a basic character, as described above. The nonesterified carboxy groups may also be salified with therapeutically active bases in the case of the vehicled substance being of a nonbasic nature.

The use of alginic esters as a vehicle is particularly useful in ophthalmology, where it is possible to observe a particular compatibility of the new products with the corneal epithelium, thereby showing excellent tolerability, with no sensitization effects. Furthermore, when the medicaments are administered in the form of concentrated solutions with elastic-viscous characteristics or in solid form, it is possible to obtain on the corneal epithelium perfectly transparent homogenous and stable films with excellent adhesive qualities, guaranteeing prolonged bioavailabilitiy of the drug and therefore representing first class products with a retard effect. These ophthalmic medicaments are especially valuable in the veterinary field, considering that there are no veterinary preparations for ophthalmic use containing chemical agents. Usually, preparations intended for human use are utilized, and sometimes these do not guarantee a specific range of action or they do not allow for the particular conditions in which treatment must take place. This is the case, for example, of infective keratoconjunctivitis, pink eye or IBK, an infection which usually afflicts cattle, sheep and goats. Presumably for these three species there exist specific etiological factors. More precisely, in cattle the main microorganism involved seems to be *Moraxella bovis* (even though other agents of a viral origin should not be excluded, such as for example the Rinotracheitis virus, Micoplasma in sheep, Rickettsia and Chlamydia, Rickettsia in goats).

The disease occurs in an acute form and tends to spread rapidly: in the initial stages the symptomatology is characterised by blepharospasm and excessive watering of the eye, followed by purulent exudate, conjunctivitis and keratitis, often associated with high temperature, reduced appetite and milk production. Particularly serious are the corneal lesions which in their final stages may even result in perforation of the cornea itself. The clinical course varies from a few days to several weeks. A wide range of treatments based on chemical agents are used, administered both topically (often associated with steroid anti-inflammatories), and systemically. Examples of these are: tetracyclines, such as oxytetracycline, penicillins, such as cloxacillin and benzylpenicillin, sulfamides, polimyxin B (associated with miconazole and prednisolone), chloramphenicol and tilosina. Topical treatment of the disease, despite its apparent simplicity, is still an open problem, since for one reason or another, with the ophthalmic preparations in use up till now it has not been possible to obtain therapeutically efficient concentrations of antibiotic or sulfamidic in the lachrymal secretion. This is quite understandable in the case of solutions, if one thinks of the mainly inclined position of the head in the above mentioned animals, but it is also true of the semisolid medicaments since the excipients commonly used in them do not have the necessary qualities of adhesion to the corneal surface, lacking generally a sufficiently high concentration of active substance and being unable to obtain perfect distribution of the same (presence of a distribution gradient). These drawbacks to conventional collyriums in use in ophthalmology have for example been described by Slatter et al. in "Austr.vet.J.," 1982, 59 (3), pp. 69–72.

By using the esters of the present invention these difficulties can be overcome. The presence of the alginic ester as vehicle in ophthalmic drugs allows for the formulation of excellent preparations with no concentration gradient of the active substance and therefore with perfect homogeneity, perfect transparency and excellent adhesion to the corneal epithelium, with no sensitisation effects, with excellent vehicling of the active substance and possibly with a retard effect.

The above mentioned properties of the new medicaments may of course also be used to advantage in other fields other than ophthalmology: they may be applied in dermatology and in infections of the mucus, for example of the mouth. They may also be used to obtain a systemic effect thanks to transcutaneous absorption, for example in suppositories. All these applications are possible both in human and veterinary medicine. In human medicine the new medicaments are particularly suitable for use in pediatrics. The present invention therefore also includes in particular any one of these therapeutic applications.

For the sake of brevity, in the following text reference to the active substance of component (1) according to the invention should also be understood to mean the association or mixture of two or more active substances.

Component (1) as described above is a pharmacologically active substance. Such substances can first of all be generically catalogued with respect to their use in the various fields of therapy, beginning with the distinction between human and veterinary medicine and then specifying the various sectors of application with respect to the organs or tissues to be treated, such as ophthalmology, dermatology, otolaryngology, gynecology, angiology, neurology or any type of pathology of internal organs which can be treated by topical applications, for example rectal applications. According to one particular aspect of the present invention, the pharmacologically active substance (1) is first and foremost a substance for ophthalmic use. According to a further criterion the pharmacologically active substance (1) should be identified according to its effect and can therefore, for example, be an anesthetic, analgesic, anti-inflammatory, vasoconstrictor, antibacterial, antiviral drug. In the field of ophthalmology, the indications can be in particular for example: miotic, anti-inflammatory, wound healing and antimicrobial effects.

Component (1) may also be, according to the invention, an association of two or more active substances, as contained in many known medicaments. For example, in ophthalmology, it is possible to associate an antibiotic with an antiphlogistic and a vasoconstrictor or several antibiotics with one or more antiphlogistics, or one or more antibiotics with a mydriatic or a myotic or wound healer or an anti-allergic agent etc. For example it is possible to use the following associations of ophthalmic drugs: kanamycin+phenylephrine+dexamethasone phosphate, kanamycin+betamethasone phosphate+-phenylephrine, or similar associations with other antibiotics used in ophthalmology, such as rolitetracycline, neomycin, gentamycin, tetracycline.

In dermatology it is possible to use as active component (1) associations of various antibiotics, such as erythromycin, gentamycin, neomycin, gramicidin, polymyxin B, between themselves, or such antibiotics with anti-inflammatory agents, for example corticosteroids, for example hydrocortisone+neomycin, hydrocortisone+neomycin+polymyxin B+gramicidin, dexamethasone+neomycin, fluorometholone+neomycin, prednisolone+neomycin, triamcinolone+-neomycin+gramicidin+nystatin, or any other association used in conventional dermatological preparations. The associations of various active substances are not of course limited to these fields, but in all the above sectors of medicine it is possible to use associations similar to those already in use for the pharmaceutical preparations known to the art.

In the case refered to above wherein the substance (1) is of a basic character, the salts formed with a partial alginic ester may be of various types. That is, all of the remaining carboxy groups may be salified or only an aliquot portion thereof, and esters are therefore obtained—acid salts, or esters—neutral salts. The number of acid groups to be kept free may be important for the preparation of medicaments with a particular pH.

According to one particular aspect of the invention it is possible to prepare the medicaments of this type starting with the previously isolated and possibly purified salts and, in their solid anydrous state, as an amorphous powder, which on contact with the tissue to be treated constitute a concentrated aqueous solution of a gelatinous character with viscous consistency and elastic properties. These qualities are maintained also at stronger dilutions and it is therefore possible to use, instead of the above anhydrous salts, solutions more or less concentrated in water or saline, possibly with the addition of other excipients or additives, such as other mineral salts to regulate the PH and osmotic pressure. It is also possible of course to use salts for the preparation of gels, inserts, creams or ointments, containing other excipients or ingredients used in traditional formulations of these pharmaceutical preparations.

According to a main aspect of the invention however, the medicaments containing the alginic ester or its salts are used with therapeutically active or inactive substances as a vehicle alone (excepting possibly an aqueous solvent). Also included in the invention are the mixtures obtainable from all types of medicaments described here and also mixtures of such medicaments, as well as possibly mixtures of the new alginic esters with free alginic acid or mixtures of their salts, for example sodium salts.

Examples of pharmacologically active substances (1) to be used in ophthalmic medicaments according to the invention are: basic and non basic antibiotics, for example aminoglycosides, macrolides, tetracyclines and peptides, such as for example gentamycin, neomycin, streptomycin, dihydrostreptomycin, kanamycin, amikacin, tobramycin, spectinomycin, erythromycin, oleandomycin, carbomycin, spiramycin, oxytetracycline, rolitetracycline, bacitracin, polymyxin B, gramicidin, colistin, cloramphenicol, lincomycin, vancomycin, novobiocin, ristocetin, clindamycin, amphotericin B, griseofulvin, nystatin and possibly their salts, such as sulfates or nitrates, or associations of these between themselves or with other active principles, such as for example those mentioned hereafter.

Other ophthalmic drugs to be used to advantage according to the present invention are: other anti-infectives such as diethylcarbamazine, mebendazole, sulfamidics such as sulfacetamide, sulfadiazine, sulfisoxazole; antivirals and anti-tumorals such as iododeoxyuridine, adenine arabinoside, trifluorothymidine, acyclovir, ethyldeoxyuridine, bromovinyldeoxyuridine, 5-iodo-5'-amino-2', 5'-did ridine; steroid anti-inflammatory agents, such as dexamethasone, hydrocortisone, prednisolone, fluorometholone, medrisone and possibly their esters, for example phosphoric acid esters; nonsteroid anti-inflammatories, for example indomethacin, oxyphenbutazone, flurbiprofen; wound healers such as epidermal growth factor EGF; local anesthetics, such as Benoxinate, proparacaine and possibly their salts; cholinergic agonists such as pilocarpine, methacholine, carbamylcholine, aceclidine, physostigmine, neostigmine, demecarium and possibly their salts; cholinergic antagonist drugs such as atropine and its salts; adrenergic agonist drugs such as noradrenaline, adrenalin, naphazoline, methoxamine and possibly their salts; adrenergic antagonist drugs such as propanolol, timolol, pindolol, bupranolol, atenolol, metoprolol, oxprenolol, practolol, butoxamine, sotalol, butethrin, labetalol and possibly their salts.

Associations or mixtures of such drugs between themselves and possibly with other principles may also be used as component (1) according to the invention. If instead of only one active substance (1), associations of active substances are used, such as those reported above, the salts of the basic active substances and the partial ester of alginic acid may be mixed salts of one or more of such basic substances or possibly mixed salts of this type with a certain number of further acid groups of the polysaccharide salified with the above mentioned metals or bases. For example it is possible to prepare salts of a partial ester of alginic acid with a pharmacologically inactive alcohol, for example a lower alkanol, and with a certain percentage of the acid groups salified with the antibiotic kanamycin, another percentage salified with the vasoconstrictor phenylephrine, and a remaining percentage of the free acid groups being possibly salified for example with sodium or one of the other above mentioned metals It is possible to mix this type of mixed salt too with free alginic acid or its fractions or their metal salts, as indicated above for the medicaments constituted by salts of only one active substance with the aforesaid polysaccharide esters.

Examples of active substances to be used on their own or in association between themselves or with other active principles in dermatology are: therapeutic agents such as anti-infective, antibiotic, antimicrobial, anti-inflammatory, cytostatic, cytotoxic, antiviral, anesthetic agents, and prophylactic agents, such as sun shields, deodorants, antiseptics and disinfectants. Of the antibiotics, we mention erythromycin, bacitracin, gentamycin, neomycin, aureomycin, gramicidin and associations of the same, antibacterials and disinfectants, nitrofurazone, mafenide, chlorhexidine, and 8-hydroxyquinoline derivatives and possibly their salts; anti-inflammatories, above all corticosteroids such as prednisolone, dexamethasone, flumethasone, clobetasol, acetonide of triamcinolone, betamethasone or their esters, such as valerianates, benzoates, dipropionates; of the cytotoxics, fluorouracil, methotrexate, podophyllin; of the anesthetics, dibucaine, lidocaine, benzocaine.

This list is of course only for exemplary purposes and any other agents described in literature may be used.

From the examples discussed for ophthalmology and dermatology it is possible to determine by analogy which medicaments according to the present invention are to be used in the other fields of medicine mentioned above, such as otolaryngology or odontology or in internal medicine. For example, in endocrinology, it is possible to use preparations absorbed intradermally or through the mucus, for example by rectal or nasal absorption, such as nasal sprays or preparations for inhalation into the oral cavity or pharynx. These preparations may therefore be for example anti-inflammatories, or vasoconstrictors or vasopressors such as those already mentioned for ophthalmology, vitamins, antibiotics, such as those mentioned above, hormones, chemotherapeutics, antibacterials, etc., again as mentioned above for use in dermatology.

Methods of Preparation for the Alginic Esters

According to the chemically new and original procedure of the present invention, the alginic acid esters may be prepared to advantage starting with quaternary ammonium salts of alginic acid with an alkylating agent in a preferably aprotic organic solvent, such as dialkylsulfoxides, dialkylcarboxamides, such as in particular lower alkyl dialkylsulfoxides, above all dimethylsulfoxide, and lower alkyl dialkylamides of lower aliphatic acids, such as dimethyl or diethyl formamide or dimethyl or diethylacetamide. It is possible, however, to use other solvents which are not-always aprotic, such as alcohols, ethers, ketones, esters, especially aliphatic or heterocyclic alcohols and ketones with a low boiling point, such as hexafluoroisopropanol and trifluoroethanol. The reaction is brought about preferably at a temperature of between about 0° and 100° C., and especially between about 25° and 75°, for example at about 30°.

Esterification is carried out preferably by gradually adding the alkylating agent to the above mentioned ammonium salt dissolved in one of the solvents mentioned, for example in dimethylsulfoxide. As alkylating agents, those mentioned above can be used, especially hydrocarbyl halides, for example alkyl halides.

The preferred esterification process, therefore, comprises reacting, in an organic solvent, a quaternary ammonium salt of alginic acid with a stoichiometric quantity of a compound of the formula $$A-X$$

wherein A is selected from the group consisting of an aliphatic, araliphatic, cycloaliphatic, aliphatic-cycloaliphatic and heterocyclic radicals and X is a halogen atom, and wherein said stoichiometric quantity of A—X is determined by the degree of esterification desired.

As starting quaternary ammonium salts it is preferable to use lower ammonium tetraalkylates, the alkyl groups having preferably between 1 and 6 carbon atoms. Mostly, the alginate of tetrabutylammonium is used. These quaternary ammonium salts can be prepared by reacting a metal salt of alginic acid, preferably one of those mentioned above, especially sodium or potassium salt, in aqueous solution with a sulfonic resin salified with the quaternary ammonium base. The tetraalkylammonium alginates deriving from lower alkyls, especially alkyls with between 1 and 6 carbon atoms, are new and form another object of the present invention. Unexpectedly, these salts proved to be soluble in the above aprotic solvents, and esterification of alginic acid according to the aforesaid new procedure is therefore made particularly easy and gives abundant yields. Only by using this procedure, therefore, is it possible to exactly determine the number of carboxy groups of alginic acid to be esterified.

One variation of the previously specified procedure consists in reacting a potassium or sodium salt of alginic acid, suspended in a suitable solution such as dimethylsulfoxide, with a suitable alkylating agent in the presence of a catalyzing quantity of a quaternary ammonium salt, such as tetrabutylammonium iodide. The new procedure makes it possible to obtain, as already stated, the total esters of alginic acid and also substituted alcohols such as glycols, which were previously unobtainable.

To prepare new esters according to the present invention it is possible to use alginic acids of any origin, such as for example the acids extracted from the above mentioned natural starting materials. The preparation of these acids is described in literature: it is preferable to use purified alginic acids.

In the partial esters of the present invention it is possible to salify all the remaining carboxy groups or only part of these, dosing the base quantity so as to obtain the desired stoichiometric degree of salification. By correctly gauging the degree of salification it is possible to obtain esters with a wide range of different dissociation constants, thereby giving the desired pH in solutions or "in situ" at the moment of therapeutic application.

The present invention also includes modifications of the preparation procedures of the new esters and their salts, in which a procedure is interupted at any stage or which start with an intermediate compound followed by the remaining stages, or in which the starting products are formed in situ.

The invention is illustrated by the following Examples, which do not in any way limit its scope.

Example 1—Preparation of the tetrabutylammonium salt of alginic acid 10 m.Eq. of a sodium salt of alginic acid, corresponding to 2 g. of dry compound, are solubilized in 300 ml of distilled water. The solution is then passed through a thermostatic column at 4° C. containing 15 ml of sulfonic resin (Dowex 50×8) in the form of tetrabutylammonium. The sodium-free eluate is frozen and freeze-dried.

Yield 3.3 g.

Example 2—Preparation of the (partial) ethyl ester of alginic acid—10% of the carboxy groups esterified—90% of the carboxy groups salified 10 g (23.9 m.Eq.) of the tetrabutylammonium salt of alginic acid (prepared from alginic acid obtained from Laminaria hyperborea) are solubilized in 400 ml of DMSO at 25° C. 0.377 g (2.39 m.Eq.) of ethyl iodide are added. The solution is well agitated for 12 hours at 30° C.

a) To completely convert the carboxy salts of tetrabutylammonium residues to sodium salt form, to the resulting solution is added 2.5 g of NaCl dissolved in 50 ml of distilled $H_2O$, cooling it from the outside in a bath of $H_2O$/ice. The solution is slowly poured by regular drops and under agitation in 2000 ml of ethyl acetate. The precipitate is separated by filtration, washed three times with 100 ml of acetone/$H_2O$ 5:1 and 3 times with 100 ml of pure acetone, then vacuum dried. Yield: 6 g.

b) To convert the carboxy salts of tetrabutylammonium residues to calcium salt form, the procedure is as above, substituting calcium chloride for the sodium chloride. Yield: 6.1 g.

Quantitative determination of the ester groups is carried out by the saponification method described on pages 169–172 of "Quantitative organic analysis via functional groups", 4th Edition, John Wiley and Sons Publication.

Example 3—Preparation of the (partial) ethyl ester of alginic acid—30% of the carboxy groups esterified—70% of the carboxy groups salified 10 g (23.9 m.Eq.) of the tetrabutylammonium salt of alginic acid (prepared from alginic acid obtained from Ascophyllum nodosum) are solubilized in 400 ml of DMSO at 25° C. 1.31 g (7.18 m.Eq.) of ethyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation in 2000 ml of ethyl acetate. The precipitate is separated by filtration, washed three times with 100 ml of acetone/$H_2O$ 5:1 and 3 times with 100 ml of pure acetone, then vacuum dried. Yield: 5 g.

b) To convert the carboxy salt of tetrabutylammonium residues to calcium salts, the procedure is as above, substituting calcium chloride for the sodium chloride. Yield: 5.1 g.

Quantitative determination of the ester groups is carried out by the saponification method described on pages 169-172 of "Quantitative organic analysis via functional groups", 4th Edition, John Wiley and Sons Publication.

Example 4—Preparation of the (partial) ethyl ester of alginic acid—50% of the carboxy groups esterified—50% of the carboxy groups salified 10 g (23.9 m.Eq.) of the tetrabutylammonium salt of alginic acid (prepared from alginic acid obtained from *Macrocystis pyrifera*) are solubilized in 400 ml of DMSO at 25° C. 1.88 g (11.9 m.Eq.) of ethyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation in 2000 ml of ethyl acetate. The precipitate is separated by filtration, washed three times with 100 ml of acetone/$H_2O$ 5:1 and 3 times with 100 ml of pure acetone, then vacuum dried. Yield: 4.5 g.

b) To convert the carboxy salt of tetrabutylammonium residues to calcium salts, the procedure is as above, substituting calcium chloride for the sodium chloride. Yield: 4.6 g.

Quantitative determination of the ester groups is carried out by the saponification method described on pages 169-172 of "Quantitative organic analysis via functional groups", 4th Edition, John Wiley and Sons Publication.

Example 5—Preparation of the (partial) ethyl ester of alginic acid—70% of the carboxy groups esterified—30% of the carboxy groups salified 10 g (23.9 m.Eq.) of the tetrabutylammonium salt of alginic acid (prepared from alginic acid obtained from *Laminaria hyperborea*) are solubilized in 400 ml of DMSO at 25°C. 2.64 g (16.7 m.Eq.) of ethyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation in 2000 ml of ethyl acetate. The precipitate is separated by filtration, washed three times with 100 ml of acetone/$H_2O$ 5:1 and 3 times with 100 ml of pure acetone, then vacuum dried. Yield: 4 g.

b) To convert the carboxy salt of tetrabutylammonium residues to calcium salts, the procedure is as above, substituting calcium chloride for the sodium chloride. Yield: 4.2 g.

Quantitative determination of the ester groups is carried out by the saponification method described on pages 169-172 of "Quantitative organic analysis via functional groups", 4th Edition, John Wiley and Sons Publication.

Example 6—Preparation of the (partial) ethyl ester of alginic acid—90% of the carboxy groups esterified—10% of the carboxy groups salified 10 g (23.9 m.Eq.) of the tetrabutylammonium salt of alginic acid (prepared from alginic acid obtained from *Macrocystis pyrifera*) are solubilized in 400 ml of DMSO at 25° C. 3.39 g (21,5 m.Eq.) of ethyl iodide are added. The solution is well agitated for 12 hours at 30° C.

a) For complete conversion of the carboxy salts of tetrabutylammonium residues to sodium salt, to the resulting solution is added 2,5 g of NaCl dissolved in 50 ml of. distilled $H_2O$, cooled from the outside with a bath of $H_2O$/ice. The solution is slowly poured by regular drops and under agitation in 2000 ml of ethyl acetate. The precipitate is separated by filtration, washed 3 times with 100 ml of acetone/$H_2O$ 5:1 and 3 times with 100 ml of pure acetone, then vacuum dried. Yield: 5.5 g.

b) To convert the carboxy salt of tetrabutylammonium residues to calcium salts, the procedure is as above, substituting calcium chloride for the sodium chloride. Yield: 5.6 g.

Quantitative determination of the ester groups is carried out by the saponification method described on pages 169-172 of "Quantitative organic analysis via functional groups", 4th Edition, John Wiley and Sons Publication.

Example 7—Preparation of the (partial) isopropyl ester of alginic acid—90% of the carboxy groups esterified—10% of the carboxy groups salified 10 g (23.9 m.Eq.) of the tetrabutylammonium salt of alginic acid (prepared from alginic acid obtained from *Ascophyllum nodosum*) are solubilized in 400 ml of DMSO at 25° C. 3.73 g (21.5 m.Eq.) of isopropyl iodide are added.

The solution is well agitated for 12 hours at 30 a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation in 2000 ml of ethyl acetate. The precipitate is separated by filtration, washed 3 times with 100 ml of acetone/$H_2O$ 5:1 and 3 times with 100 ml of pure acetone, then vacuum dried. Yield: 4.2 g.

b) To convert the carboxy salt of tetrabutylammonium residues to calcium salts, the procedure is as above, substituting calcium chloride for the sodium chloride. Yield: 4 g.

Quantitative determination of the ester groups is carried out by the saponification method described on pages 169-172 of "Quantitative organic analysis via functional groups", 4th Edition, John Wiley and Sons Publication.

Example 8—Preparation of the (partial) isopropyl ester of alginic acid—70% of the carboxy groups esterified—30% of the carboxy groups salified 10 g (23.9 m.Eq.) of the tetrabutylammonium salt of alginic acid (prepared from alginic acid obtained from *Laminaria hyperborea*) are solubilized in 400 ml of DMSO at 25° C. 2.9 g (16.7 m.Eq.) of isopropyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled H₂O, cooled from the outside with a bath of H₂O/ice. The solution is slowly poured by regular drops and under agitation into 2000 ml of ethyl acetate. The precipitate is separated by filtration, washed 3 times with 100 ml of acetone/ H₂O 5:1 and 3 times with 100 ml of pure acetone, then vacuum dried. Yield: 4 g.

b) To convert the carboxy salts of tetrabutylammonium residues to calcium salts, the procedure is as above, substituting calcium chloride for the sodium chloride. Yield: 3.8 g.

Quantitative determination of the ester groups is carried out by the saponification method described on pages 169–172 of "Quantitative organic analysis via functional groups", 4th Edition, John Wiley and Sons Publication.

Example 9—Preparation of the (partial) isopropyl ester of alginic acid—50% of the carboxy groups esterified—50% of the carboxy groups salified 10 g (23.9 m.Eq.) of the tetrabutylammonium salt of alginic acid (prepared from alginic acid obtained from *Macrocystis pyrifera*) are solubilized in 400 ml of DMSO at 25 C. 2.07 g (11.9 m.Eq.) of isopropyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled H₂O, cooled from the outside with a bath of H₂O/ice. The solution is slowly poured by regular drops and under agitation into 2000 ml of ethyl acetate. The precipitate is separated by filtration, washed 3 times with 100 ml of acetone/H₂O 5:1 and 3 times with 100 ml of pure acetone, then vacuum dried. Yield: 4.2 g.

b) To convert the carboxy salt of tetrabutylammonium residues to calcium salts, the procedure is as above, substituting calcium chloride for the sodium chloride. Yield: 4.2 g.

Quantitative determination of the ester groups is carried out by the saponification method described on pages 169–172 of "Quantitative organic analysis functional groups", 4th Edition, John Wiley and Sons Publication.

Example 10—Preparation of the (partial) isopropyl ester of alginic acid—30% of the carboxy groups esterified—70% of the carboxy groups salified 10 g (23.9 m.Eq.) of the tetrabutylammonium salt of alginic acid (prepared from alginic acid obtained from *Ascophyllum nodosum*) are solubilized in 400 ml of DMSO at 25° C. 1.24 g (7.18 m.Eq.) of isopropyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled H₂O, cooled from the outside with a bath of H₂O/ice. The solution is slowly poured by regular drops and under agitation into 2000 ml of ethyl acetate. The precipitate is separated by filtration, washed 3 times with 100 ml of acetone/H₂O 5:1 and 3 times with 100 ml of pure acetone, then vacuum dried. Yield: 5.5 g.

b) To convert the carboxy salt of tetrabutylammonium residues to calcium salts, the procedure is as above, substituting calcium chloride for the sodium chloride. Yield: 5.4 g.

Quantitative determination of the ester groups is carried out by the saponification method described on pages 169–172 of "Quantitative organic analysis via functional groups", 4th Edition, John Wiley and Sons Publication.

Example 11—Preparation of the (partial) isopropyl ester of alginic acid—10% of the carboxy groups esterified—90% of the carboxy groups salified 10 g (23.9 m.Eq.) of the tetrabutylammonium salt of alginic acid (prepared from alginic acid obtained from *Laminaria hyperborea*) are solubilized in 400 ml of DMSO at 25° C. 0.42 g (2.3 m.Eq.) of isopropyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled H₂O, cooled from the outside with a bath of H₂O/ice. The solution is slowly poured by regular drops and under agitation in 2000 ml of ethyl acetate. The precipitate is separated by filtration, washed 3 times with 100 ml of acetone/H₂O 5:1 and 3 times with 100 ml of pure acetone, then vacuum dried. Yield: 5.8 g.

b) To convert the carboxy salt of tetrabutylammonium residues to calcium salts, the procedure is as above, substituting calcium chloride for the sodium chloride. Yield: 5.8 g.

Quantitative determination of the ester groups is carried out by the saponification method described on pages 169–172 of "Quantitative organic analysis via functional groups", 4th Edition, John Wiley and Sons Publication.

Example 12—Preparation of the (partial) terbutyl ester alginic acid—90% of the carboxy groups esterified—10% of the carboxy groups salified 10 g (23.9 m.Eq.) of the tetrabutylammonium salt of alginic acid (prepared from alginic acid obtained from *Ascophyllum nodosum*) are solubilized in 400 ml of DMSO at 25° C. 4.1 g (21.5 m.Eq.) of terbutyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled H₂O, cooled from the outside with a bath of H₂O/ice. The solution is slowly poured by regular drops and under agitation into 2000 ml of ethyl acetate. The precipitate is separated by filtration, washed 3 times with 100 ml of acetone/H₂O 5:1 and 3 times with 100 ml of pure acetone, then vacuum dried. Yield: 4 g.

b) To convert the carboxy salt of tetrabutylammonium residues to calcium salts, the procedure is as above, substituting calcium chloride for the sodium chloride. Yield: 4.1 g.

Quantitative determination of the ester groups is carried out by the saponification method described on pages 169–172 of "Quantitative organic analysis via functional groups", 4th Edition, John Wiley and Sons Publication.

Example 13—Preparation of the (partial) terbutyl ester of alginic acid—70% of the carboxy groups esterified—30% of the carboxy groups salified 10 g (23.9 m.Eq.) of the tetrabutylammonium salt of alginic acid (prepared from alginic acid obtained from *Laminaria hyperborea*) are solubilized in 400 ml of DMSO at 25° C. 3.14 g (16.7 m.Eq.) of terbutyl iodide are added.

The solution is well agitated for 12 hours at 30° C.

a) For complete conversion of the carboxy salts of tetrabutylammonium residues to sodium salt, to the resulting solution is added 2,5 g of NaCl dissolved in 50 ml of distilled $H_2O$, cooled from the outside with a bath of $H_2O$/ice. The solution is slowly poured by regular drops and under agitation in 2000 ml of ethyl acetate. The precipitate is separated by filtration, washed 3 times with 100 ml of acetone/$H_2O$ 5:1 vacuum dried. Yield: 5 g.

b) To convert the carboxy salt of tetrabutylammonium residues in calcium salts, the procedure is as above, substituting calcium chloride for the sodium chloride. Yield: 5 g.

Quantitative determination of the ester groups is carried out by the saponification method described on pages 169-172 of "Quantitative organic analysis via functional groups", 4th Edition, John Wiley and Sons Publication.

Example 14—Preparation of the (partial) terbutyl ester of alginic acid—50% of the carboxy groups esterified—50% of the carboxy groups salified 10 g (23.9 m.Eq.) of the tetrabutylammonium salt of alginic acid (prepared from alginic acid obtained from *Macrocystis pyrifera*) are solubilized in 400 ml of DMSO at 25° C. 2.25 g (11.9 m.Eq.) of terbutyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 5.4 g.

b) To convert the carboxy salt of tetrabutylammonium residues to calcium salts, the procedure is as above, substituting calcium chloride for the sodium chloride. Yield: 5.4 g.

Quantitative determination of the ester groups is carried out by the saponification method described on pages 169-172 of "Quantitative organic analysis via functional groups", 4th Edition, John Wiley and Sons Publication.

Example 15—Preparation of the (partial) terbutyl ester of alginic acid—30% of the carboxy groups esterified—70% of the carboxy groups salified 10 g (23.9 m.Eq.) of the tetrabutylammonium salt of alginic acid (prepared from alginic acid obtained from *Laminaria hyperborea*) are solubilized in 400 ml of DMSO at 25° C. 1.34 g (7.18 m.Eq.) of terbutyl iodide are added.

The solution is well agitated for 12 hours at 30° C.

For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 5.5 g.

b) To convert the carboxy salt of tetrabutylammonium residues to calcium salts, the procedure is as above, substituting calcium chloride for the sodium chloride. Yield: 5.7 g.

Quantitative determination of the ester groups is carried out by the saponification method described on pages 169-172 of "Quantitative organic analysis via functional groups", 4th Edition, John Wiley and Sons Publication.

Example 16—Preparation of the (partial) terbutyl ester of alginic acid—10% of the carboxy groups esterified—90% of the carboxy groups salified 10 g (23.9 m.Eq.) of the tetrabutylammonium salt of alginic acid (prepared from alginic acid obtained from *Macrocystis pyrifera*) are solubilized in 400 ml of DMSO at 25° C. 0.45 g (2.39 m.Eq.) of terbutyl iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 5 g.

b) To convert the carboxy salt of tetrabutylammonium residues to calcium salts, the procedure is as above, substituting calcium chloride for the sodium chloride. Yield: 5 g.

Quantitative determination of the ester groups is carried out by the saponification method described on pages 169-172 of "Quantitative organic analysis via functional groups", 4th Edition, John Wiley and Sons Publication.

Example 17—Preparation of the (partial) benzyl ester of alginic acid—90% of the carboxy groups esterified—10% of the carboxy groups salified 10 g (23.9 m.Eq.) of the tetrabutylammonium salt of alginic acid (prepared from alginic acid obtained from *Ascophyllum nodosum*) are solubilized in 400 ml of DMSO at 25° C. 3.76 g (21.5 m.Eq.) of benzyl bromide and 0.1 g of tetrabutylammonium iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 5 g.

b) To convert the carboxy salt of tetrabutylammonium residues to calcium salts, the procedure is as above, substituting calcium chloride for the sodium chloride. Yield: 5 g.

Quantitative determination of the ester groups is carried out by the saponification method described on pages 169-172 of "Quantitative organic analysis via functional groups", 4th Edition, John Wiley and Sons Publication.

Example 18—Preparation of the (partial) benzyl ester of alginic acid—70% of the carboxy groups esterified—30% of the carboxy groups salified 10 g (23.9 m.Eq.) of the tetrabutylammonium salt of alginic acid (prepared from alginic acid obtained from *Laminaria hyperborea*) are solubilized in 400 ml of DMSO at 25° C. 2.9 g (16 7 m.Eq.) of benzyl bromide and 0.1 g of tetrabutylammonium iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 4.6 g.

b) To convert the carboxy salt of tetrabutylammonium residues to calcium salts the procedure is as above, substituting calcium chloride for the sodium chloride. Yield: 4.5 g.

Quantitative determination of the ester groups is carried out by the saponification method described on pages 169-172 of "Quantitative organic analysis via functional groups", 4th Edition, John Wiley and Sons Publication.

Example 19—Preparation of the (partial) benzyl ester alginic acid—50% of the carboxy groups esterified—50% of the carboxy groups salified 10 g (23.9 m.Eq.) of the tetrabutylammonium salt of alginic acid (prepared from alginic acid obtained from *Ascophyllum nodosum*) are solubilized in 400 ml of DMSO at 25° C. 2.1 g (11.9 m.Eq.) of benzyl bromide and 0.1 g of tetrabutylammonium iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 4.2 g.

b) To convert the carboxy salt of tetrabutylammonium residues to calcium salts, the procedure is as above, substituting calcium chloride for the sodium chloride. Yield: 4.3 g.

Quantitative determination of the ester groups is carried out by the saponification method described on pages 169-172 of "Quantitative organic analysis via functional groups", 4th Edition, John Wiley and Sons Publication.

Example 20—Preparation of the (partial) benzyl ester of alginic acid—30% of the carboxy groups esterified—70% of the carboxy groups salified 10 g (23.9 m.Eq.) of the tetrabutylammonium salt of alginic acid (prepared from alginic acid obtained from *Ascophyllum nodosum*) are solubilized in 400 ml of DMSO at 25° C. 1.25 g (7.18 m.Eq.) of benzyl bromide and 0.1 g of tetrabutylammonium iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops and under agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 6 g.

b) To convert the carboxy salt of tetrabutylammonium residues to calcium salts, the procedure is as above, substituting calcium chloride for the sodium chloride. Yield: 6.1 g.

Quantitative determination of the ester groups is carried out by the saponification method described on pages 169-172 of "Quantitative organic analysis via functional groups", 4th Edition, John Wiley and Sons Publication.

Example 21—Preparation of the (partial) benzyl ester of alginic acid—10% of the carboxy groups esterified—90% of the carboxy groups salified 10 g (23.9 m.Eq.) of the tetrabutylammonium salt of alginic acid (prepared from alginic acid obtained from *Macrocystis pyrifera*) are solubilized in 400 ml of DMSO at 25° C. 0.42 g (2.39 m.Eq.) of benzyl bromide and 0.1 g of tetrabutylammonium iodide are added.

The solution is well agitated for 12 hours at 30° C.

a) For complete conversion of the carboxy salts of tetrabutylammonium residues to sodium salt, to the resulting solution is added 2.5 g of NaCl dissolved in 50 ml of distilled $H_2O$, cooled from the outside with a bath of $H_2O$/ice. The solution is slowly poured by regular drops being kept in agitation into 2000 ml of ethyl acetate. The precipitate is separated by filtration, washed 3 times with 100 ml of acetone/$H_2O$ 5:1 and 3 times with 100 ml of pure acetone, then vacuum dried. Yield: 5 g.

b) To convert the carboxy salt of tetrabutylammonium residues to calcium salts, the procedure is as above, substituting the calcium chloride for the sodium chloride. Yield: 5 g.

Quantitative determination of the ester groups is carried out by the saponification method described on pages 169-172 of "Quantitative organic analysis via functional groups", 4th Edition, John Wiley and Sons Publication.

Example 22—Preparation of the methyl ester of alginic acid 8.35 g (20 m.Eq.) of the tetrabutylammonium salt of alginic acid (prepared from alginic acid obtained from *Ascophyllum nodosum*) are solubilized in 400 ml of DMSO at 25° C. 3.66 g (25 m.Eq.) of methyl idide are added.

The solution is well agitated for 12 hours at 30° C., and then slowly poured by regular drops and under agitation into 3.5 l of ethyl acetate (or toluene). The precipitate is filtered and then washed 4 times with ethyl acetate and lastly vacuum dried for 24 hours at 30° C. In this way 4 g of the compound named in the title are obtained.

Quantitative determination of the ester groups is carried out by the saponification method described on pages 169-172 of "Quantitative organic analysis via functional groups", 4th Edition, John Wiley and Sons Publication.

Example 23—Preparation of the benzyl ester of alginic acid 10 g (23.9 m.Eq.) of the tetrabutylammonium salt of alginic acid (prepared from alginic acid obtained from *Macrocystis pyrifera*) are solubilized in 400 ml of DMSO at 25° C. 4.45 g (26 m.Eq.) of benzyl bromide and 0.1 g of tetrabutylammonium iodide are added.

The solution is well agitated for 12 hours at 30° C., and then slowly poured by regular drops and under agitation into 3.5 l of ethyl acetate (or toluene). The precipitate is filtered and then washed 4 times with ethyl acetate and lastly vacuum dried for 24 hours at 30° C. In this way 5 g of the compound named in the title are obtained.

Quantitative determination of the ester groups is carried out by the saponification method described on pages 169-172 of "Quantitative organic analysis via functional groups", 4th Edition, John Wiley and Sons Publication.

Example 24—Preparation of the tert-butyl ester of alginic acid 10 g (23.9 %.Eq.) of the tetrabutylammonium salt of alginic acid (prepared from alginic acid obtained from *Laminaria hyperborea*) are solubilized in 400 ml of DMSO at 25° C. 4.8 g (26 m.Eq.) of tert-butyl iodide are added.

The solution is well agitated for 12 hours at 30° C., and then slowly poured by regular drops and under agitation into 3.5 l of ethyl acetate (or toluene). The precipitate is filtered and then washed 4 times with ethyl acetate and lastly vacuum dried for 24 hours at 30° C. In this way 3.8 g of the compound named in the title are obtained.

Quantitative determination of the ester groups is carried out by the saponification method described on pages 169-172 of "Quantitative organic analysis via functional groups", 4th Edition, John Wiley and Sons Publication.

Example 25—Preparation of the isopropyl ester of alginic acid 10 g (23,9 m.Eq.) of the tetrabutylammonium salt of alginic acid (prepared from alginic acid obtained from *Laminaria hyperborea*) are solubilized in 400 ml of DMSO at 25° C. 4.4 g (26 m.Eq.) of isopropyl iodide are added. The solution is well agitated for 12 hours at 30° C., and then slowly poured by regular drops and under agitation into 3.5 l of ethyl acetate (or toluene). The precipitate is filtered and then washed 4 times with ethyl acetate and lastly vacuum dried for 24 hours at 30° C. In this way 4.5 g of the compound named in the title are obtained.

Quantitative determination of the ester groups is carried out by the saponification method described on pages 169-172 of "Quantitative organic analysis via functional groups", 4th Edition, John Wiley and Sons Publication.

Example 26—Preparation of the ethyl ester of alginic acid 10 g (23.9 m.Eq.) of the tetrabutylammonium salt of alginic acid (prepared from alginic acid obtained from *Ascophyllum nodosum*) are solubilized in 400 ml of DMSO at 25° C. 4 g (26 m.Eq.) of ethyl iodide are added. The solution is well agitated for 12 hours at 30° C., and then slowly poured by regular drops and under agitation into 3.5 l of ethyl acetate (or toluene). The precipitate is filtered and then washed 4 times with ethyl acetate and lastly vacuum dried for 24 hours at 30° C. In this way 4.5 g of the compound named in the title are obtained.

Quantitative determination of the ester groups is carried out by the saponification method described on pages 169-172 of "Quantitative organic analysis via functional groups", 4th Edition, John Wiley and Sons Publication.

Example 26A—Preparation of the amikacin salt of alginic acid partially esterified with ethanol—75% of carboxylic groups esterified with ethanol—25% of carboxylic groups salified with amikacin 147 mg of amikacin (1 m.Eq.) are solubilized in 20 ml of water.

0.81 g of a 75% ethyl ester of alginic acid and sodium salt at 25% (corresponding to 1 m.Eq. of a monomeric unit relative to the non-esterified carboxyl), are solubilized in 400 ml of water. The solution is eluted in a thermostatic column at 20° and containing 2 ml of sulfonic resin (Dowes $50 \times 8$) in $H^+$ form.

The sodium-free eluate is gathered under agitation in the solution of amikacin base. The resulting solution is instantly frozen and freeze-dried.

Microbiological determination carried out on *St. aureus* ATCC 29737 in comparison to standard amikacin, shows a content of 8.5% in weight of amikacin base, corresponding to the theoretically calculated value.

Example 26B—Preparation of erythromycin salt of alginic acid partially esterified with ethanol—75% of carboxylic groups esterified with ethanol—25% of carboxylic groups salified with erythromycin.

0.81 g of a 75% ethyl ester of alginic acid and sodium salt at 25% (corresponding to 1 m.Eq. of a monomeric unit relative to the non-esterified carboxyl), are solubilized in 400 ml of water. The solution is eluted in a thermostatic column at 20° containing 2 ml of sulfonic resin (Dowex $50 \times 8$) in $H^+$ form.

To the sodium-free eluate are added 734 mg of erythromycin base (1 m.E.q.). The resulting solution is instantly frozen and freeze-dried.

Microbiological determination on *St. aureus* ATCC 6538 in comparison to standard erythromycin, shows a content of 31.7% in weight of erythromycin base, corresponding to the theoretically calculated weight.

Example 26C—Preparation of streptomycine salt of alginic acid partially esterified with ethanol—75% of carboxylic groups esterified with ethanol—25% of carboxylic groups salified with streptomycine.

243 mg of streptomycine sulphate (1 m.Eq.) are solubilized in 20 ml of water. The solution of eluted in a thermostatic column at 5° containing 2 ml of quaternary ammonium resin (Dowex $1 \times 8$) in $OH^-$ form.

The sulphate-free eluate is gathered in a thermostatic container at a temperature of 5°.

0.81 g of a 75% ethyl ester of alginic acid and 25% sodium salt (corresponding to 1 m.Eq. of a monomeric unit relative to the non-esterified carboxyl), are solubilized in 400 ml of water. The solution is eluted in a thermostatic column at 20° and containing 2 ml of sulphonic resin (Dowex 50×8) in H+ form.

The sodium-free eluate is gathered under agitation in the solution of streptomycine base. The resulting solution is instantly frozen and freeze-dried.

Microbiological determination on *B. subtilis* ATCC 6633 in comparison with streptomycine standard, shows a content of 10.9% in weight of streptomycine base, corresponding to the theoretically calculated content.

Example 26D—Preparation of the (partial and mixed ethanol and fluorocortisone esters ($C_{21}$) of alginic acid—40% of carboxylic groups esterified with ethanol—20% of carboxylic groups esterified with fluorocortisone ($C_{21}$)—40% of salified carboxylic groups (Na)

8.35 g of the tetrabutylammonium salt of alginic acid (prepared from *Laminaria hyperborea*) corresponding to 20 m.Eq. of a monomeric unit are solubilized in 350 ml of dimethylsulfoxide at 25°, 0.62 g (4 m.Eq.) of ethyl iodide are added and the solution is kept for 24 hours at 300.

0.89 g (2 m.Eq.) of 9α-fluoro-21-bromo-4-pregnene-11β, 17α-diol-3, 20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml acetone and finally vacuum dried for eight hours at 30°.

3.5 g of the alginic acid partially esterified with mixed ethanol and fluorocortisone as in the title are obtained. Quantitative determination of fluorocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028–1030 (1961)].

Example 26E—Preparation of the (partial) fluorocortisone esters ($C_{21}$) of alginic acid—20% of esterified carboxylic groups—80% of salified carboxylic groups (Na)

4.18 g of the tetrabutylammonium salt of alginic acid (prepared from *Laminaria hyperborea*) corresponding to 10 m.Eq. of a monomeric unit are solubilized in 210 ml of dimethylsulfoxide at 25°, 0.89 g (2 m.Eq.) of 9Oα-fluoro-21-bromo-4-pregnene-11β, 17α-diol-3,20-dione are added and the resulting solution is kept for 12 hours at 30°.

A solution is then added containing 62 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°. 1.5 g of the partial fluorocortisone compound in the title are obtained.

Quantitative determination of fluorocortisone after mild alkaline hydrolysis with hydroalcoholic solution of $Na_2CO_3$ and extraction with chloroform, is carried out according to British Pharmacopea, 1980, p. 196.

Example 26F—Preparation of the (mixed) ethanol and hydrocortisone esters ($C_{21}$) of alginic acid—80% of carboxylic groups esterified with ethanol—20% of carboxylic groups esterified with hydrocortisone ($C_{21}$).

4.18 g of the tetrabutylammonium salt of alginic acid (prepared from *Laminaria hyperborea*) corresponding to 10 m Eq. of a monomeric unit are solubilized in 210 ml of dimethylsulfoxide at 25°, 1.25 g (8 m.Eq.) of ethyl iodide are added and the solution is kept at 30° for 12 hours.

0.85 g (2 m.Eq.) of 21-bromo-4-pregnene-11β, 17α-diol-3,20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

1.8 g of the mixed ethanol and hydrocortisone ester compound in the title are obtained. Quantitative determination of hydrocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028–1030)].

Example 26G—Preparation of the (partial) hydrocortisone esters ($C_{21}$) of alginic acid—20% of esterified carboxylic groups—80% of salified carboxylic groups (Na)

8.35 g of the tetrabutylammonium salt of alginic acid (prepared from *Microcystis pyrifera*) corresponding to 20 m.Eq. of a monomeric unit are solubilized in 350 ml of dimethylsulfoxide at 25°, 0.850 g. (2 m.Eq.) of 21-bromo-4-pregnene-11β, 17α-diol-3,20-dione are added and the resulting solution is kept for 24 hours at 30°.

A solution is then added containing 100 ml of water and 5 g of sodium chloride and the resulting mixture is slowly poured into 2,000 ml of acetone under contant agitation. A precipitate is formed which is filtered and washed three times with 100 ml of acetone/water 5:1 and three times with acetone and finally vacuum dried for eight hours at 30°.

The product is then dissolved in 300 ml of water containing 1% of sodium chloride and the solution is slowly poured into 1,500 ml of acetone under constant agitation. A precipitate is formed which is filtered and washed twice with 100 ml of acetone/water 5:1 and three times with 100 ml of acetone and finally vacuum dried for 24 hours at 30°.

3 g of the alginic acid partially esterified with hydrocortisone compound in the title are obtained.

Quantitative determination of hydrocortisone after mild alkaline hydrolysis with hydroalcoholic solution of $Na_2CO_3$ and extraction with chloroform, is carried out according to British Pharmacopea, 1980, p. 224.

Example 26H—Preparation of the (mixed) ethanol and fluorocortisone ester ($C_{21}$) of alginic acid—80% of carboxylic groups esterified with ethanol—20% of carboxylic groups esterified with fluorocortisone ($C_{21}$)

4.18 g of the tetrabutylammonium salt of alginic acid (prepared from *Macrocystis pyrifera*) corresponding to 10 m.Eq. of a monomeric unit are solubilized in 210 ml of dimethylsulfoxide at 25°, 1.25 g (8 m.Eq.) of ethyl iodide are added and the solution is kept for 24 hours at 30°.

0.89 g (2 m.Eq.) of 9α- fluoro-21-bromo-4-pregnene-11β, 17α-diol-3,20-dione are added and the solution is kept for 24 hours at 30°.

A solution is then added containing 100 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

1.7 g of the mixed ethanol and fluorocortisone ester compound featured in the title are obtained.

Quantitative determination of fluorocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028-1030 (1961)].

Example 26I—Preparation of the (partial and mixed) ethanol and hydrocortisone ester ($C_{21}$) of alginic acid—40% of carboxylic groups esterified with ethanol—20% of carboxylic groups esterified with hydrocortisone ($C_{21}$)—40% of salified carboxylic groups (Na)

4.18 g of the tetrabutylammonium salt of alginic acid (prepared from *Macrocystis pyrifera*) corresponding to 10 m.Eq. of a monomeric unit are solubilized in 210 ml of dimethylsulfoxide at 25°, 0.62 g (4 m.Eq.) of ethyl iodide are added and the solution is kept for 24 hours at 30°.

0.85 g (2 m.Eq.) of 21-bromo-4-pregnene-11β, 17α-diol-3,20-dione are added and the solution is kept for 24 hours at 30°.

A solution is then added containing 200 ml of water and 5 g of sodium chloride and the resulting mixture is slowly poured into 2,000 ml of acetone under constant agitation. A precipitate is formed which is filtered and washed three times with 100 ml of acetone/water 5:1 and three times with 100 ml of acetone and finally vacuum dried for eight hours at 30°.

1.7 g of the partial and mixed ethanol and hydrocortisone ester compound in the title are obtained.

Quantitative determination of hydrocortisone, after mild alkaline hydrolysis with hydroalcoholic solution of $Na_2CO_3$ and extraction with chloroform, is carried out according to British Pharmacopea, 1980.

Quantitative determination of the ethoxyls is carried out according to R. H. Cundiff and P. C. Markunas [Anal. Chem. 33, 1028-1030 (1961)].

Pharmaceautical Preparations of the Alginic Esters

One object of the present invention is the pharmaceutical preparations containing one or more alginic acid esters as described above or medicaments resulting from the association of one such ester with a pharmacologically active substance as described above, that is medicaments in which the alginic ester acts as a vehicle for the active substance.

The pharmaceutical preparations containing therapeutically active alginic esters, possibly in the form of the above medicaments resulting from the association of components (1) and (2), contain the usual excipients and may be destined for oral, rectal, parenteral, subcutaneous, local or intradermal use. They are therefore in solid or semisolid form, for example pills, tablets, gelatin capsules, capsules, suppositories, soft gelatin capsules. For parenteral and subcutaneous use it is possible to use forms intended for intramuscular and intradermal administration, or suitable for intravenous infusion or injection. It is therefore possible to present active compounds as solutions or as freeze-dried powders to unite with one or more excipients or diluents acceptable from a pharmaceutical point of view and convenient for the above uses and of compatible osmolarity with the physiological fluids. For local use, preparations in spray form should be considered, for example nasal sprays, creams or ointments for topical use or suitably prepared plasters for intradermal administration.

The preparations of the invention may be intended for administration to man or animal. These contain preferably between 0.01% and 10% of active component for the solutions, sprays, ointments and creams and between 1% and 100% and preferably between 5% and 50% of the active compound for the preparations in solid form. The dosage to be administered depends on the particular indication, on the desired effect and chosen administration route. The daily dosage of these preparations may be estimated from those in use for the corresponding known preparations for the corresponding cures of the therapeutically active alcohol, whose action is to be exploited. In this way, for example, the dosage of an alginic ester with cortisone may be derived from its content in this same steroid and from its usual dosage in the known pharmaceutical preparations.

One particular form of pharmaceutical preparations is represented by the abovesaid medicaments consituted by the association of an alginic ester and an active substance, for example for topical use. These may also be in solid form, for example as freeze-dried powders containing only the two components (1) and (2) as a mixture or separate. When these medicaments in solid form come into contact with the epithelium to be treated, they form more or less concentrated solutions according to the nature of the particular epithelium to be treated, with the same characteristics as the solution previously prepared in vitro and which represent another particularly important aspect of the present invention. These solutions are preferably made with distilled water or sterile saline and preferably contain no other pharmaceutical vehicle except the alginic ester or one of its salts.

The concentrations of these solutions may also vary greatly, for example between 0.01 and 75% both for each of the two components considered separately, and for their mixtures or salts. Preference is given in particular to solutions with a pronounced elastic-viscous character, for example with a content of between 10% and 90% of the medicament or of each of its components.

Of particular importance are medicaments of this type, both in anhydrous form (freeze-dried powders) or as concentrated solutions or diluted in water or saline, possibly with the addition of additive or auxiliary substances, such as in particular disinfectant substances or mineral salts acting as buffers or others, used for ophthalmic purposes.

Of the medicaments of the invention, those to be chosen, as the case may be, are those with a degree of acidity suitable for the zone to which they are to be applied, that is with a physiologically tolerable PH. Adjustment of the PH, for example in the above mentioned salts of the alginic acid esters with a basic active substance, may be effected by suitably regulating the quantitites of polysaccharide, its salts and of the basic substance itself. In this way, for example, if the acidity of an alginic ester salt with a basic substance is too high, the excess of free acid groups can be neutralized with the above mentioned inorganic bases, for example with sodium, potassium or ammonium hydrate.

Preparation of the salts according to the invention may be carried out in the known way, by bringing into contact solutions or aqueous suspensions or in organic solvents of the two components (1) and (2) and possibly of bases or basic salts of the above mentioned alkaline or alkaline earth metals or magnesium or aluminium in calculated quantities and isolating the salts in anhydrous amorphous form according to the known methods. It is possible for example to first of all prepare aqueous solutions of the two components (1) and (2), freeing these components from aqueous solutions of their salts with suitable ion-exchangers, uniting the two solutions at a low temperature, for example between 0° and 20°, if the salts thus obtained are easily soluble in water it is freeze-dried, while salts with poor solubility can be separated by centrifugation or filtration or decantation and possibly subsequently dried.

For these associated medicaments too, the dose is based on that of the active principles used singly and may therefore be easily determined by those skilled in the art, considering the doses recommended for the corresponding known medicaments.

In the cosmetic articles according to the invention the alginic esters and their salts are mixed with the excipients commonly used in this field and are for example those already listed above for the pharmaceutical preparations. Above all are used creams, ointments, lotions for topical use in which the alginic ester or one of its salts may constitute the active cosmetic principle possibly with the addition of other cosmetically active principles, such as for example steroids, for example pregnenolone, or one of the principles previously reported. In these preparations the alginic ester may be an ester with a cosmetically active alcohol, such as dexpanthenol, or also an ester with an alcohol having no cosmetic action, such as a lower aliphatic alcohol, for example one of those already quoted: the effect is due to the intrinsic cosmetic properties of the polysaccharide component, such as in the case of free alginic acid or of its salts.

The cosmetic articles may however be based on various other active principles, for example disinfectant substances, sun shields, water-repellents, regenerating or antiwrinkle substances, or odoriferous substances, especially perfumes. In this case the alginic ester itself may again be the active ingredient and derive from alcohols with these same properties, for example from higher aliphatic alcohols or terpene alcohols in the case of perfumes or act above all as vehicling substance for instance with those properties which are associated with it. Particularly important therefore are cosmetic compositions similar to the medicaments described above in which the pharmaceutically active component (1) is substituted by a cosmetological factor, and the respective salts. Use of the above esters deriving from alcohols used in the perfume industry represents a great step ahead in the advance of technique, since it allows a slow, constant and protracted release of the odoriferous principles.

The following are particular exemplary pharmaceutical Preparations according to the invention.

Formulation 1—Collirium containing cortisone of which 100 ml contain:
alginic acid partially esterified with cortisone, gr. 0.200
ethyl p. hydroxybenzoate, gr. 0.010
methyl p. hydroxybenzoate, gr. 0.050
sodium chloride, gr. 0.900
water for injectable preparations/q.b.a., ml. 100

Formulation 2—Injectable solution containing hydrocortisone of which 100 ml contain:
alginic acid partially esterified with hydrocortisone, gr. 0.1
water for injectable preparations/q.b.a., ml 100

Formulation 3—Cream containing a partial ester of alginic acid with ethyl alcohol, of which 100 gr. contain:
alginic acid partially esterified with ethyl alcohol, gr. 0.2
Polyethyleneglycol monostearate 400, gr. 10.000
Cetiol V, gr. 5.000
Lanette SX, gr. 2.000
Paraoxybenzoate of methyl, gr. 0.075
Paraoxybenzoate of propyl, gr. 0.050
Sodium dihydroacetate, gr. 0.100
Glycerine F. U., gr. 1.500
Sorbitol 70, gr. 1.500
Test cream, gr. 0.050
Water for injectable preparations/q.b.a., gr. 100.00

Medical Articles Containing the Alginic Esters

One important application of the present invention regards the sanitary and surgical articles already described, the methods for their manufacture and their use. The invention therefore includes all the articles similar to those already on the market made with alginic acid but containing an alginic ester or one of its salts in place of the free acid or one of its salts, for example inserts or ophthalmic lenses.

Completely new surgical and sanitary articles according to the present invention are represented by the esters of alginic acid regenerated as such from appropriate organic solutions and capable of being made into sheet and thread form, thus obtaining films, sheets and threads for use in surgery, as skin auxiliaries and substitutes in cases of serious damage to this organ, such as for example following burns, or as suture threads in surgical operations. The invention includes in particular these uses and a preparation procedure for such articles consisting in the formation of a solution of alginic ester or of one of its salts in an appropriate organic solvent, for example a ketone, an ester or an aprotic solvent such as an amide of a carboxylic acid, especially a dialkylamide or of an aliphatic acid with between 1 and 5 carbon atoms and deriving from alkyl groups with between 1 and 6 carbon atoms, particularly by an organic sulfoxide, that is a dialkylsulfoxide with alkyl groups with a maximum of 6 carbon atoms, such as especially dimethylsulfoxide or diethylsulfoxide and most preferably a fluorurate solvent with a low boiling point, such as especially hexafluoroisopropanol.

The invention then consists in making these solutions into sheets or threads and in removing the organic solvent by contact with another organic or aqueous solvent, capable of being mixed with the first solvent and in which the alginic ester is not soluble, especially a lower aliphatic alcohol, for example ethyl alcohol (wet spinning), or should a solvent with a fairly low boiling point have been used to prepare the solutions of alginic derivative, in removing such solvent under dry conditions with a current of gas, and especially suitably heated nitrogen (dry spinning). Excellent results can also be obtained with dry-wet spinning.

The threads obtained with the alginic acid esters may be used for the preparation of gauzes to be used for the medication of wounds and in surgery. These gauzes have the exceptional advantage of biodegradability in the organism, made possible by the naturally existing enzymes. These enzymes divide the ester into alginic acid and the corresponding alcohol, when an alginic ester deriving from a therapeutically acceptable alcohol is used, such as ethyl alcohol.

These gauzes and also the aforesaid threads may therefore also be left inside the organism after surgery, being then slowly absorbed after the previously mentioned process of degradation.

In the preparation of the aforesaid sanitary and surgical articles, it is convenient to add plasticizing materials in order to improve their mechanical characteristics, as in the case of threads, to improve their resistance to knots and tangles. Such plasticizers may be for example alkaline salts of fatty acids, for example sodium stearate or sodium palmitate, the esters of organic acids with a high number of carbon atoms, etc. Another application of the new esters is represented by the preparation of capsules for subcutaneous implantation of medicaments or of microcapsules for injection, for example by subcutaneous or intramuscular route, where their biodegradability is exploited by the esterases present in the organism.

Of great importance also is the preparation of microcapsules made with alginic esters, solving the problems previously connected with their use, up till now very limited, for the same reasons as those set out previously, opening up a wide field of application where a "retard" effect is desired after administration by injection.

A further application of the new esters in the field of medicine and surgery involves the preparation of a wide variety of solid inserts such as plates, discs, laminas, etc. substituting for those made of metal or synthetic plastic material already in use, in cases where such inserts are to be removed after a certain period of time. Preparations based on animal collagens, being of a proteinaceous nature, often give rise to unpleasant reactions, such as inflammation or rejection symptoms. In the case of alginic esters, this danger does not exist.

Part of the applications in the medical-surgical field of the new esters according to the present invention, concerns preparations using expansile material, especially in the form of sponges, for the medication of wounds or various types of lesion.

The following preparations exemplify the medical articles according to the invention containing the alginic esters.

Example 27—Preparation of films using esters of alginic acid

A solution is prepared in dimethylsulfoxide of the n-propyl ester of alginic acid with a concentration of 180 mg/ml.

By means of a stratifier, a thin layer of solution is spread on a glass sheet; the thickness must be 10 times greater than the final thickness of the film. The glass sheet is immersed in ethanol which absorbs the dimethylsulfoxide but does not solubilize the HY ester which becomes solid. The film is detached from the glass sheet, is repeatedly washed with ethanol, then with water and then again with ethanol.

The resulting sheet is dried in a press for 48 hours at 30°.

Example 28—Preparation of threads using esters of alginic acid

A solution is prepared in dimethylsulfoxide of the benzyl ester of alginic acid with a concentration of 200 mg/ml. The solution thus obtained is pressed by means of a pump through a threader with 0.5 mm holes.

The threader is immersed in ethanol/dimethylsulfoxide 80:20 (this concentration is kept constant by continuous addition of ethanol); when the solution in dimethylsulfoxide is soaked in this way it tends to lose most of the dimethylsulfoxide and the thread solidifies.

The thread is stretched while it still has a content of dimethylsulfoxide, is then repeatedly stretched and washed with ethanol. The thread is dried in nitrogen current.

Example 29—Preparation of a spongy material made with alginic esters 1 g of benzyl ester of alginic acid in which all the carboxylic groups are esterified (obtained for example as described in Example 23) are dissolved in 5 ml of dimethylsulfoxide. To each 10 ml of solution prepared, a mixture of 31.5 g of sodium chloride with a degree of granularity corresponding to 300$\mu$, 1.28 g of sodium bicarbonate and 1 g of citric acid is added and the whole is homogenized in a mixer.

The pasty mixture is stratified in various ways, for instance by means of a mange consisting of two rollers which turn opposite each other at an adjustable distance between the two. Regulating this distance the paste is passed between the rollers together with a strip of silicone paper which acts as a support to the layer of paste thus formed. The layer is cut to the desired dimensions of length and breadth, removed from the silicone, wrapped in filter paper and emerged in a suitable solvent, such as water. The sponges thus obtained are washed with a suitable solvent such as water and possibly sterilized with gamma rays.

Example 30—Preparation of a spongy material made with alginic acid esters

In the manner described in Example 29, it is possible to prepare spongy materials with other alginic acid esters. In the place of dimethylsulfoxide it is possible to use, if desired, any other solvent capable of dissolving the chosen ester. In the place of sodium chloride it is possible to use any other solid compound which is insoluble in the solvent used to dissolve the hyaluronic acid ester, but which is however soluble in the solvent used to precipiate the hyaluronic ester after the above mentioned mechanical treatment, and finally which has the correct degree of granularity to obtain the type of pores desired in the sponge material.

In the place of sodium bicarbonate and citric acid it is possible to use other couples of similar compounds, that is, compounds which react to each other in suspension or solution of the solvent used to dissolve alginic acid in such a way as to form a gas, such as carbon dioxide, which has the effect of producing a less compact spongy material. In this way it is possible to use, in the place of sodium bicarbonate, other bicarbonates or alkaline or alkaline earth carbonates and in the place of citric acid other acids in solid form, such as tartaric acid.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

We claim:

1. A pharmaceutical composition comprising, as active ingredient, an effective amount of an alginic acid partially esterified with an alcohol wherein the alcohol moiety is derived from steroidal alcohols, or a salt thereof with an inorganic or organic base; and a pharmacologically acceptable carrier.

2. The pharmaceutical compositions according to claim 1 wherein the alcohol moiety is derived from alcohols of the cortisone type.

3. The pharmaceutical compositions according to claim 1 wherein the alcohol moiety is derived from hydrocortisone.

* * * * *